United States Patent
Porat et al.

(10) Patent No.: US 8,277,441 B2
(45) Date of Patent: *Oct. 2, 2012

(54) PIEZOELECTRIC TRANSDUCER

(75) Inventors: Yariv Porat, Halfa (IL); Yoseph Tsaliah, Kiryat Blalik (IL); Eyal Doron, Kiriat-Yam (IL)

(73) Assignee: Remon Medical Technologies, Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/075,384

(22) Filed: Mar. 30, 2011

(65) Prior Publication Data

US 2011/0178578 A1      Jul. 21, 2011

Related U.S. Application Data

(63) Continuation of application No. 12/578,376, filed on Oct. 13, 2009, now Pat. No. 7,948,148, which is a continuation of application No. 10/638,405, filed on Aug. 12, 2003, now Pat. No. 7,621,905, which is a continuation of application No. 09/930,455, filed on Aug. 16, 2001, now abandoned, and a continuation-in-part of application No. 10/235,968, filed on Sep. 6, 2002, now Pat. No. 6,720,709, which is a continuation of application No. 09/691,887, filed on Oct. 20, 2000, now Pat. No. 6,504,286, which is a continuation of application No. 09/000,553, filed on Dec. 30, 1997, now Pat. No. 6,140,740.

(51) Int. Cl.
   *A61K 9/22* (2006.01)
   *H04R 17/00* (2006.01)

(52) U.S. Cl. .................. 604/891.1; 604/890.1; 367/157; 367/180

(58) Field of Classification Search .................... 604/20, 604/890.1; 367/140, 157, 180
See application file for complete search history.

(56) References Cited

U.S. PATENT DOCUMENTS

| | | | |
|---|---|---|---|
| 2,967,957 | A | 1/1961 | Massa |
| 3,568,661 | A | 3/1971 | Franklin |
| 3,676,720 | A | 7/1972 | Libby et al. |
| 3,757,770 | A | 9/1973 | Brayshaw et al. |

(Continued)

FOREIGN PATENT DOCUMENTS

| | | |
|---|---|---|
| DE | 1101331 | 4/1958 |

(Continued)

OTHER PUBLICATIONS

Blevins Ph.D. "Formulas for Natural Frequency and Mode Shape" Florida 1979; p. 240; ISBN: 1575241846.

(Continued)

*Primary Examiner* — Victoria P Shumate
(74) *Attorney, Agent, or Firm* — Faegre Baker Daniels LLP

(57) ABSTRACT

Devices and systems for transmitting information within a body are disclosed. An example system includes a signal generator configured for transmitting an acoustic interrogation signal, a sensor for sensing at least one parameter within the body and generating an electrical sensor signal, an acoustic transducer coupled to the sensor and configured to convert a received acoustic interrogation signal into an electrical signal, and a switching element adapted to modulate a reflected acoustic wave from the acoustic transducer based on the electrical sensor signal. The switching element is configured to controllably change the mechanical impedance of the acoustic transducer based a parameter of the electrical sensor signal, such as frequency.

15 Claims, 11 Drawing Sheets

U.S. PATENT DOCUMENTS

| | | | |
|---|---|---|---|
| 3,792,204 A | 2/1974 | Murayama et al. | |
| 3,798,473 A | 3/1974 | Murayama et al. | |
| 3,832,580 A | 8/1974 | Yamamuro et al. | |
| 3,894,198 A | 7/1975 | Murayama et al. | |
| 3,940,637 A | 2/1976 | Ohigashi et al. | |
| 3,978,353 A | 8/1976 | Kinoshita | |
| 4,008,408 A | 2/1977 | Kodama | |
| 4,051,455 A | 9/1977 | Fowler | |
| 4,056,742 A | 11/1977 | Tibbetts | |
| 4,064,375 A * | 12/1977 | Russell et al. | 381/190 |
| 4,096,756 A | 6/1978 | Alphonse | |
| 4,127,110 A | 11/1978 | Bullara | |
| 4,170,742 A | 10/1979 | Itagaki et al. | |
| 4,181,864 A | 1/1980 | Etzold | |
| 4,227,407 A | 10/1980 | Drost | |
| 4,281,484 A | 8/1981 | Massa | |
| 4,431,873 A | 2/1984 | Dunn et al. | |
| 4,433,400 A | 2/1984 | De Reggi et al. | |
| 4,440,983 A | 4/1984 | Facoetti et al. | |
| 4,456,850 A | 6/1984 | Inoue et al. | |
| 4,471,786 A | 9/1984 | Inagaki et al. | |
| 4,481,950 A | 11/1984 | Duggan | |
| 4,517,665 A | 5/1985 | De Reggi et al. | |
| 4,519,401 A | 5/1985 | Ko et al. | |
| 4,541,431 A | 9/1985 | Ibrahim et al. | |
| 4,558,249 A | 12/1985 | Lerch et al. | |
| 4,577,132 A | 3/1986 | Ohigashi et al. | |
| 4,580,074 A | 4/1986 | Gilman | |
| 4,593,703 A | 6/1986 | Cosman | |
| 4,600,855 A | 7/1986 | Strachan | |
| 4,642,508 A | 2/1987 | Suzuki et al. | |
| 4,653,036 A | 3/1987 | Harris et al. | |
| 4,653,508 A | 3/1987 | Cosman | |
| 4,660,568 A | 4/1987 | Cosman | |
| 4,672,976 A | 6/1987 | Kroll | |
| 4,676,255 A | 6/1987 | Cosman | |
| 4,677,337 A | 6/1987 | Kleinschmidt et al. | |
| 4,781,715 A | 11/1988 | Wurzel | |
| 4,793,825 A | 12/1988 | Benjamin et al. | |
| 4,835,435 A | 5/1989 | Yeung et al. | |
| 4,846,191 A | 7/1989 | Brockway et al. | |
| 4,911,172 A | 3/1990 | Bui et al. | |
| 4,940,052 A * | 7/1990 | Mann et al. | 607/17 |
| 4,958,100 A | 9/1990 | Crawley et al. | |
| 4,992,692 A * | 2/1991 | Dias | 310/335 |
| 5,012,815 A | 5/1991 | Bennett, Jr. et al. | |
| 5,024,224 A | 6/1991 | Engebretson | |
| 5,088,576 A | 2/1992 | Potthoff et al. | |
| 5,113,859 A | 5/1992 | Funke | |
| 5,160,870 A | 11/1992 | Carson et al. | |
| 5,178,153 A | 1/1993 | Einzig | |
| 5,283,397 A | 2/1994 | Pavlovic | |
| 5,289,821 A | 3/1994 | Swartz | |
| 5,300,875 A | 4/1994 | Tuttle | |
| 5,304,206 A * | 4/1994 | Baker et al. | 607/2 |
| 5,314,457 A | 5/1994 | Jeutter et al. | |
| 5,339,290 A | 8/1994 | Greenstein et al. | |
| 5,367,500 A | 11/1994 | Ng | |
| 5,381,067 A | 1/1995 | Greenstein et al. | |
| 5,381,386 A | 1/1995 | Lum et al. | |
| 5,410,587 A | 4/1995 | Grunwell | |
| 5,411,551 A | 5/1995 | Winston et al. | |
| 5,423,334 A | 6/1995 | Jordan | |
| 5,438,553 A | 8/1995 | Wilson et al. | |
| 5,476,488 A | 12/1995 | Morgan et al. | |
| 5,483,501 A | 1/1996 | Park et al. | |
| 5,488,954 A | 2/1996 | Sleva et al. | |
| 5,495,137 A | 2/1996 | Park et al. | |
| 5,507,786 A * | 4/1996 | Morgan et al. | 607/27 |
| 5,554,177 A | 9/1996 | Kieval et al. | |
| 5,562,714 A | 10/1996 | Grevious | |
| 5,571,152 A | 11/1996 | Chen et al. | |
| 5,628,782 A | 5/1997 | Myers | |
| 5,679,026 A | 10/1997 | Fain et al. | |
| 5,704,352 A | 1/1998 | Tremblay et al. | |
| 5,733,313 A | 3/1998 | Barreras, Sr. et al. | |
| 5,735,887 A | 4/1998 | Barreras, Sr. et al. | |
| 5,741,316 A | 4/1998 | Chen et al. | |
| 5,749,909 A * | 5/1998 | Schroeppel et al. | 607/33 |
| 5,757,104 A | 5/1998 | Getman et al. | |
| 5,792,195 A | 8/1998 | Carlson et al. | |
| 5,807,258 A | 9/1998 | Cimochowski et al. | |
| 5,825,117 A | 10/1998 | Ossmann et al. | |
| 5,832,924 A | 11/1998 | Archibald et al. | |
| 5,833,603 A | 11/1998 | Kovacs et al. | |
| 5,843,135 A | 12/1998 | Weijand et al. | |
| 5,870,351 A | 2/1999 | Ladabaum et al. | |
| 5,873,835 A | 2/1999 | Hastings et al. | |
| 5,879,283 A | 3/1999 | Adams et al. | |
| 5,935,081 A | 8/1999 | Kadhiresan | |
| 5,956,292 A | 9/1999 | Bernstein | |
| 5,957,950 A | 9/1999 | Mockros et al. | |
| 5,967,986 A | 10/1999 | Cimochowski et al. | |
| 6,044,298 A | 3/2000 | Salo et al. | |
| 6,053,873 A | 4/2000 | Govari et al. | |
| 6,058,329 A | 5/2000 | Salo et al. | |
| 6,068,589 A | 5/2000 | Neukermans | |
| 6,082,367 A | 7/2000 | Greeninger et al. | |
| 6,140,740 A * | 10/2000 | Porat et al. | 310/322 |
| 6,141,588 A | 10/2000 | Cox et al. | |
| 6,185,452 B1 | 2/2001 | Schulman et al. | |
| 6,223,081 B1 | 4/2001 | Kerver | |
| 6,353,277 B1 | 3/2002 | Hahn-Jose | |
| 6,409,675 B1 | 6/2002 | Turcott | |
| 6,475,170 B1 | 11/2002 | Doron et al. | |
| 6,477,406 B1 | 11/2002 | Turcott | |
| 6,480,733 B1 | 11/2002 | Turcott | |
| 6,486,588 B2 * | 11/2002 | Doron et al. | 310/322 |
| 6,504,286 B1 * | 1/2003 | Porat et al. | 310/324 |
| 6,504,289 B2 | 1/2003 | Toda et al. | |
| 6,527,729 B1 | 3/2003 | Turcott | |
| 6,537,200 B2 | 3/2003 | Leysieffer et al. | |
| 6,554,761 B1 | 4/2003 | Puria et al. | |
| 6,575,894 B2 | 6/2003 | Leysieffer et al. | |
| 6,600,949 B1 | 7/2003 | Turcott | |
| 6,628,989 B1 | 9/2003 | Penner et al. | |
| 6,629,922 B1 | 10/2003 | Puria et al. | |
| 6,629,951 B2 | 10/2003 | Laufer et al. | |
| 6,643,548 B1 | 11/2003 | Mai et al. | |
| 6,645,145 B1 | 11/2003 | Dreschel et al. | |
| 6,654,638 B1 | 11/2003 | Sweeney | |
| 6,671,550 B2 | 12/2003 | Iaizzo et al. | |
| 6,697,674 B2 | 2/2004 | Leysieffer | |
| 6,720,709 B2 * | 4/2004 | Porat et al. | 310/324 |
| 6,740,076 B2 | 5/2004 | Hoben et al. | |
| 6,741,714 B2 | 5/2004 | Jensen | |
| 6,763,722 B2 | 7/2004 | Fjield et al. | |
| 6,764,446 B2 | 7/2004 | Wolinsky et al. | |
| 6,772,490 B2 | 8/2004 | Toda | |
| 6,792,308 B2 | 9/2004 | Corbucci | |
| 6,999,685 B1 | 2/2006 | Kawase et al. | |
| 7,015,392 B1 | 3/2006 | Dickenson | |
| 7,016,739 B2 | 3/2006 | Bange et al. | |
| 7,024,248 B2 | 4/2006 | Penner et al. | |
| 7,035,684 B2 | 4/2006 | Lee | |
| 7,107,103 B2 | 9/2006 | Schulman et al. | |
| 7,114,502 B2 | 10/2006 | Schulman et al. | |
| 7,115,096 B2 | 10/2006 | Siejko et al. | |
| 7,118,531 B2 | 10/2006 | Krill | |
| 7,123,962 B2 | 10/2006 | Siejko et al. | |
| 7,127,290 B2 | 10/2006 | Girouard et al. | |
| 7,176,602 B2 | 2/2007 | Schlenke | |
| 7,198,603 B2 | 4/2007 | Penner et al. | |
| 7,220,232 B2 | 5/2007 | Suorsa et al. | |
| 7,228,175 B2 | 6/2007 | Jain et al. | |
| 7,236,821 B2 | 6/2007 | Cates | |
| 7,248,923 B2 | 7/2007 | Maile et al. | |
| 7,260,429 B2 | 8/2007 | Siejko et al. | |
| 7,273,457 B2 | 9/2007 | Penner | |
| 7,283,874 B2 | 10/2007 | Penner | |
| 7,335,169 B2 | 2/2008 | Thompson et al. | |
| 7,431,699 B2 | 10/2008 | Siejko et al. | |
| 7,522,962 B1 | 4/2009 | Doran et al. | |
| 7,621,905 B2 * | 11/2009 | Penner et al. | 604/891.1 |
| 7,634,318 B2 | 12/2009 | Tran et al. | |
| 7,912,548 B2 | 3/2011 | Mi et al. | |
| 7,948,148 B2 | 5/2011 | Porat et al. | |

| | | | |
|---|---|---|---|
| 7,949,396 B2 | 5/2011 | Mi et al. | |
| 2001/0026111 A1* | 10/2001 | Doron et al. | 310/322 |
| 2002/0045921 A1* | 4/2002 | Wolinsky et al. | 607/61 |
| 2002/0177782 A1 | 11/2002 | Penner | |
| 2003/0006673 A1* | 1/2003 | Porat et al. | 310/324 |
| 2003/0014080 A1 | 1/2003 | Baudino | |
| 2003/0036746 A1* | 2/2003 | Penner et al. | 604/891.1 |
| 2004/0032187 A1* | 2/2004 | Penner et al. | 310/311 |
| 2004/0106954 A1 | 6/2004 | Whitehurst et al. | |
| 2004/0122484 A1 | 6/2004 | Hatlestad et al. | |
| 2004/0127792 A1 | 7/2004 | Siejko et al. | |
| 2004/0138572 A1 | 7/2004 | Thiagarajan | |
| 2004/0172079 A1 | 9/2004 | Chinchoy | |
| 2004/0204744 A1 | 10/2004 | Penner | |
| 2004/0230249 A1 | 11/2004 | Haefner | |
| 2004/0260214 A1 | 12/2004 | Echt et al. | |
| 2005/0131472 A1 | 6/2005 | Ding et al. | |
| 2005/0137490 A1 | 6/2005 | Scheiner et al. | |
| 2005/0149138 A1 | 7/2005 | Min et al. | |
| 2006/0009818 A1 | 1/2006 | Von Arx et al. | |
| 2006/0136004 A1 | 6/2006 | Cowan | |
| 2006/0142819 A1* | 6/2006 | Penner et al. | 607/60 |
| 2006/0149329 A1 | 7/2006 | Penner | |
| 2007/0049977 A1 | 3/2007 | Von Arx et al. | |
| 2007/0055184 A1 | 3/2007 | Echt et al. | |
| 2007/0093875 A1 | 4/2007 | Chavan et al. | |
| 2007/0142728 A1 | 6/2007 | Penner | |
| 2008/0021289 A1 | 1/2008 | Zhang et al. | |
| 2008/0021509 A1 | 1/2008 | Mi et al. | |
| 2008/0021510 A1 | 1/2008 | Mi et al. | |
| 2008/0033497 A1 | 2/2008 | Bulkes et al. | |
| 2008/0103553 A1* | 5/2008 | Penner et al. | 607/60 |
| 2008/0191581 A9* | 8/2008 | Penner et al. | 310/311 |
| 2008/0195186 A1 | 8/2008 | Li et al. | |
| 2010/0004718 A1* | 1/2010 | Doron et al. | 607/60 |
| 2010/0049269 A1 | 2/2010 | Tran et al. | |
| 2010/0094105 A1* | 4/2010 | Porat et al. | 600/309 |

FOREIGN PATENT DOCUMENTS

| | | |
|---|---|---|
| DE | 3222349 | 1/1984 |
| EP | 0897690 | 8/1997 |
| EP | 0798016 | 10/1997 |
| EP | 1151719 | 4/2001 |
| EP | 1422970 | 5/2004 |
| JP | 57-177735 | 11/1982 |
| JP | 62-102734 | 5/1987 |
| JP | 05-023323 | 2/1993 |
| JP | 05-284599 | 10/1993 |
| JP | 07-046694 | 2/1995 |
| JP | 07-301670 | 11/1995 |
| JP | 09-237398 | 9/1997 |
| JP | 2001-514455 | 9/2001 |
| JP | 2002-528887 | 9/2002 |
| JP | 2003-079621 | 3/2003 |
| JP | 2004-147319 | 5/2004 |
| RU | 2239383 | 11/2004 |
| WO | WO83/03345 | 10/1983 |
| WO | WO97/01986 | 1/1997 |
| WO | WO97/33513 | 9/1997 |
| WO | WO97/35636 | 10/1997 |
| WO | WO97/47236 | 12/1997 |
| WO | WO98/26716 | 6/1998 |
| WO | WO98/29030 | 7/1998 |
| WO | WO98/51025 | 11/1998 |
| WO | WO99/26530 | 6/1999 |
| WO | WO 99/34453 A1 | 7/1999 |
| WO | WO99/59460 | 11/1999 |
| WO | WO00/16686 | 3/2000 |
| WO | WO03/068047 | 8/2003 |
| WO | WO2004/091719 | 10/2004 |
| WO | WO2006/010010 | 1/2006 |
| WO | WO2006/056857 | 6/2006 |
| WO | WO2006/069215 | 6/2006 |
| WO | WO2007/025163 | 3/2007 |
| WO | WO2007/047966 | 4/2007 |
| WO | WO2008/011570 | 1/2008 |
| WO | WO2008/011577 | 1/2008 |

OTHER PUBLICATIONS

C. Hierold et al. (Germany 1998) "Implantable Low Power Integrated Pressure Sensor System for Minimal Invasive Telemetric Patient Monitoring" IEEE pp. 568-573.

Cassereau et al. "Time Reversal of Ultrasonic Fields Part 3: Theory of the Closed TimeReversal Cavity" IEEE Transactions on Ultrasonics Ferroelectrics and Frequency Control vol. 39 No. 5, Sep. 1992 pp. 579-592.

Dipl.Ing Torsten Eggers et al. (Germany) "Implantable Telemetric Endosystem (ITES)" IMSAS Institut Fur MikrosensorenAktuatoren UndSysteme, 1998, 2 pp.

ER. Cosman et al. (Massachussetts Apr. 1979) "A Telemetric Pressure Sensor for Ventricular Shunt Systems" Surgical Neurology vol. 11 No. 4, pp. 287-294.

Fink et al. "Time Reversal Acoustics" 2004 IEEE Transactions on Ultrasonics Ferroelectrics and Frequency Control Joint 50th Anniversary Conference Ultrasonics Symposium pp. 850-859.

Fink "Time Reversal of Ultrasonic Fields Part 1: Basic Principles" IEEE Transactions on Ultrasonics Ferroelectrics and Frequency Control vol. 39 No. 5, Sep. 1992, pp. 555-566.

G. W. H. Schurink et al. (1998) "Late Endoleak after Endovascular Therapy for Abdominal Aortic Aneurysm" Eur. J. Vasc. Endovasc. Surg. vol. 17, pp. 448-450.

GH White et al. (1997) "Endoleak Following Endoluminal Repair of AAA: Management Options and Patient Outcomes" J. Endovasc Surg. p. I45.

Karl E. Richard et al. (Germany Jan. 1999) "First clinical results with a telemetric shunt-integrated ICP-sensor" Neurological Research vol. 21, pp. 117-120.

Prof. Dr. Johannes Zacheja et al. (Germany Sep. 1996) "An Implantable Microsystem for Biomedical Applications" Micro System Technologies 96 pp. 717-722.

S. K. Gupta et al. (1999) "Use of a Piezoelectric Film Sensor for Monitoring Vascular Grafts" The American Journal of Surgery vol. 160, pp. 182-186.

T. Chuter et al. (Sweden Jan. 1997) "Aneurysm Pressure following Endovascular Exclusion" Eur. J. Vasc. Endovasc. Surg. vol. 13, pp. 85-87.

T.A. Cochran et al. (1990) "Aortic Aneurysm Abdominal" Current Therapy in Adult Medicine Fourth Edition, pp. 509-517.

Wu et al. "Time Reversal of Ultrasonic Fields Part 2: Experimental Results" IEEE Transactions on Ultrasonics Ferroelectrics and Frequency Control vol. 39 No. 5, Sep. 1992, pp. 567-578.

Z. Tang et al. (May 1995) "Data Transmission from an Implantable Biotelemeter by LoadShift Keying Using Circuit Configuration Modulator" IEEE Transactions on Biomedical Engineering vol. 42 No. 5, pp. 524-528.

* cited by examiner

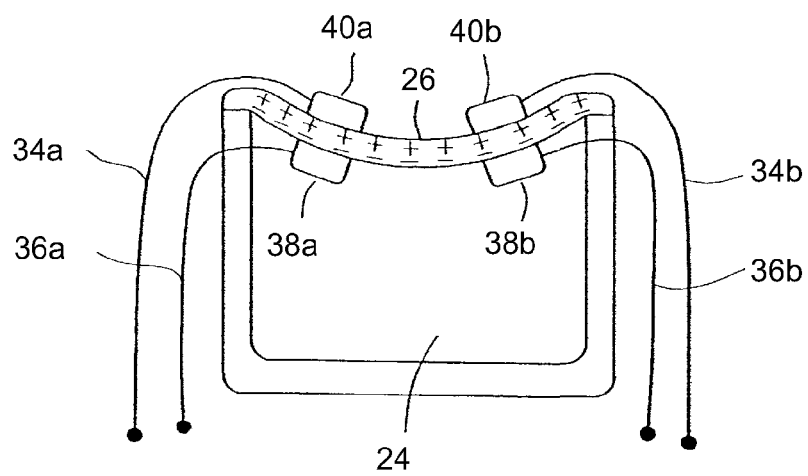
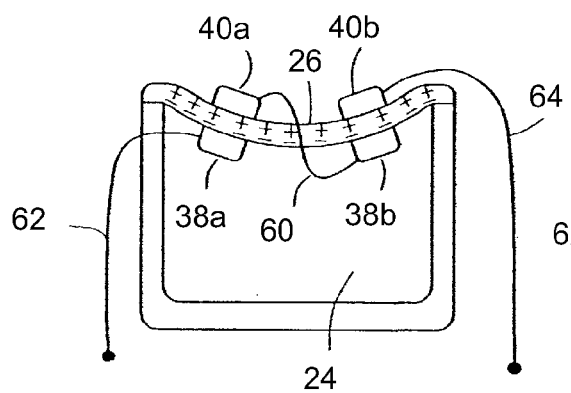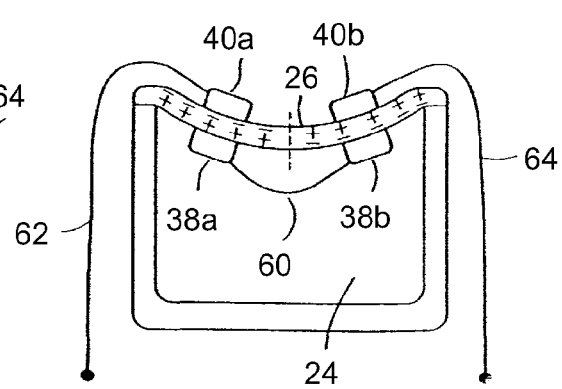

PIEZOELECTRIC TRANSDUCER

CROSS REFERENCE TO RELATED APPLICATIONS

This Application is a continuation of U.S. Application Ser. No. 12/578,376, filed Oct. 13, 2009, now U.S. Pat. No. 7,948,148, which is a continuation of U.S. Application Ser. No. 10/638,405, filed Aug. 12, 2003, now U.S. Pat. No. 7,621,905, which is a continuation of U.S. Application Ser. No. 09/930,455, filed Aug. 16, 2001, now abandoned, and which is also a continuation-in-part of U.S. Application Ser. No. 10/235,968, filed Sep. 6, 2002, now U.S. Pat. No. 6,720,709, which is a continuation of U.S. Application Ser. No. 09/691,887, filed Oct. 20, 2000, now U.S. Pat. No. 6,504,286, which is a continuation of U.S. Application Ser. No. 09/000,553, filed Dec. 30, 1997, now U.S. Pat. No. 6,140,740, all of which are incorporated herein by reference in their entireties for all purposes.

FIELD AND BACKGROUND OF THE INVENTION

The present invention relates to a device for intrabody delivery of molecules, to a method and system of utilizing same and to a method of fabricating same. More particularly, embodiments of the present invention relate to a drug delivery device which utilizes an acoustic transducer for generating an electrical activation signal from an acoustic signal received thereby.

The efficacy of drug treatment is oftentimes dependent upon the mode of drug delivery.

Localized drug delivery is oftentimes preferred since it traverses limitations associated with systemic drug delivery including rapid drug inactivation and/or ineffectual drug concentrations at the site of treatment. In addition, in some cases, systemic drug delivery can lead to undesired cytotoxic effects at tissue regions other than that to be treated.

Since localized intrabody delivery of medication is central to efficient medical treatment, attempts have been made to design and fabricate intrabody delivery devices which are capable of controlled and localized release of a wide variety of molecules including, but not limited to, drugs and other therapeutics.

Controlled release polymeric devices have been designed to provide drug release over a period of time via diffusion of the drug out of the polymer and/or degradation of the polymer over the desired time period following administration to the patient. Although these devices enable localized drug delivery, their relatively simple design is limited in that it does not enable accurate and controlled delivery of the drug.

U.S. Pat. No. 5,490,962 to Cima, et al. discloses the use of three dimensional printing methods to make more complex devices which provide release over a desired time frame, of one or more drugs. Although the general procedure for making a complex device is described, specific designs are not detailed.

U.S. Pat. No. 4,003,379 to Ellinwood describes an implantable electromechanically driven device that includes a flexible retractable walled container, which receives medication from a storage area via an inlet and then dispenses the medication into the body via an outlet.

U.S. Pat. Nos. 4,146,029 and 3,692,027 to Ellinwood disclose self-powered medication systems that have programmable miniaturized dispensing means.

U.S. Pat. No. 4,360,019 to Jassawalla discloses an implantable infusion device that includes an actuating means for delivery of the drug through a catheter. The actuating means includes a solenoid driven miniature pump.

Since such devices include miniature power-driven mechanical parts which are required to operate in the body, i.e., they must retract, dispense, or pump, they are complicated and subject to frequent breakdowns. Moreover, due to complexity and size restrictions, they are unsuitable for delivery of more than a few drugs or drug mixtures at a time.

U.S. Pat. Nos. 6,123,861 and 5,797,898 both to Santini, Jr., et al. disclose microchip devices which control both the rate and time of release of multiple chemical substances either in a continuous or a pulsatile manner. Such microchip devices employ a reservoir cap which is fabricated of a material that either degrades or allows the molecules to diffuse passively out of the reservoir over time or materials that oxidize and dissolve upon application of an electric potential. Release from the microchip device can be controlled by a preprogrammed microprocessor, via a radiofrequency (RF) activation signal, or by biosensors.

Although the microchip device described by Santini, Jr., et al. presents substantial improvements over other prior art devices, it suffers from several inherent limitations which will be described in detail hereinbelow.

There is thus a widely recognized need for, and it would be highly advantageous to have, a delivery device and methods of fabricating and utilizing same which device can be used for accurate and timely delivery of a drug or drugs within a body tissue region devoid of the above limitation.

The present invention also relates to an acoustic transducer and, in particular, to a miniature flexural piezoelectric transducer for receiving acoustic energy transmitted from a remote source and converting such energy into electrical power for activating an electronic circuit. Further, the present invention relates to a miniature flexural piezoelectric transmitter for transmitting acoustic information by modulating the reflection of an external impinging acoustic wave.

The prior art provides various examples of piezoelectric transducers. Examples of such piezoelectric transducers are disclosed in U.S. Pat. Nos. 3,792,204; 4,793,825; 3,894,198; 3,798,473; and 4,600,855.

However, none of the prior art references provide a miniature flexural piezoelectric transducer specifically tailored so as to allow the usage of low frequency acoustic signals for vibrating the piezoelectric layer at its resonant frequency, wherein substantially low frequency signals herein refer to signals having a wavelength that is much larger than the dimensions of the transducer. Further, none of the prior art references provide a miniature transducer having electrodes specifically shaped so as to maximize the electrical output of the transducer. Further, none of the above references provide a transducer element which may be integrally manufactured with any combination of electronic circuits by using photolithographic and microelectronics technologies.

Further, the prior art fails to provide a miniature flexural piezoelectric transmitter which modulates the reflected acoustic wave by controllably changing the mechanical impedance of the piezoelectric layer according to a message signal received from an electronic component such as a sensor. Further, the prior art fails to provide such transmitter wherein the piezoelectric layer is electrically connected to a switching element, the switching element for alternately changing the electrical connections of the transmitter so as to alternately change the mechanical impedance of the piezoelectric layer. Further, the prior art fails to provide such transducer wherein the mechanical impedance of the piezoelectric layer is controlled by providing a plurality of electrodes attached thereto, the electrodes being electrically interconnected in parallel and anti-parallel electrical connections. Further, the prior art fails to provide such transmitter wherein the piezoelectric layer features different polarities at distinct portions thereof. Further, the prior art fails to provide such transmitter which includes a chamber containing a low pressure gas for enabling asymmetrical fluctuations of the piezoelectric layer. Further, the prior art fails to provide such transmitter having a two-ply piezoelectric layer.

SUMMARY OF THE INVENTION

According to one aspect of the present invention there is provided a device for controlled release of molecules comprising: (a) a device body having at least one reservoir therein for containing the molecules, the at least one reservoir being formed with a barrier impermeable to the molecules thereby preventing release thereof from the at least one reservoir; and (b) at least one acoustic transducer being attached to, or forming a part of, the device body, the at least one acoustic transducer being for converting an acoustic signal received thereby into an electrical signal, the electrical signal leading to barrier permeabilization and therefore release of the molecules from the at least one reservoir.

According to an additional aspect of the present invention there is provided a system for localized delivery of molecules within the body comprising: (a) an intrabody implantable device including: (i) a device body having at least one reservoir therein for containing the molecules, the at least one reservoir being formed with a barrier impermeable to the molecules thereby preventing release thereof from the at least one reservoir; and (ii) at least one acoustic transducer being attached to, or forming a part of, the device body, the at least one acoustic transducer being for converting an acoustic signal received thereby into an electrical signal, the electrical signal leading to barrier permeabilization and therefore release of the molecules from the at least one reservoir; and (b) an extracorporeal unit for generating the acoustic signal.

According to another aspect of the present invention there is provided a method of delivering molecules to a specific body region, the method comprising: (a) implanting within the body region a device including: (i) a device body having at least one reservoir therein containing the molecules, the at least one reservoir being formed with a barrier impermeable to the molecules thereby preventing release thereof from the at least one reservoir; and (ii) at least one acoustic transducer being attached to, or forming a part of, the device body, the at least one acoustic transducer being for converting an acoustic signal received thereby into an electrical signal, the electrical signal leading to barrier permeabilization and therefore release of the molecules from the at least one reservoir; and (b) extracorporeally irradiating the body with an acoustic signal thereby causing the subsequent release of the molecules from the at least one reservoir.

According to further features in preferred embodiments of the invention described below, the device further comprising a cathode, and an anode, whereas the electrical signal generates an electric potential between the cathode and the anode leading to permeabilization of the barrier and release of the molecules from the at least one reservoir.

According to still further features in the described preferred embodiments the anode is attached to or forms at least a part of the barrier.

According to still further features in the described preferred embodiments the electrical signal directly generates the electric potential between the cathode and the anode.

According to still further features in the described preferred embodiments the device further comprising a power source for generating the electric potential between the cathode and the anode upon receiving the electrical signal from the at least one acoustic transducer.

According to still further features in the described preferred embodiments the at least one acoustic transducer serves as an acoustic switch.

According to still further features in the described preferred embodiments permeabilization of the barrier is effected by at least partial disintegration thereof.

According to still further features in the described preferred embodiments a type or duration of the electrical signal controls a degree of permeabilization of the barrier and thus an amount of the molecules released.

According to still further features in the described preferred embodiments the device includes a plurality of reservoirs.

According to still further features in the described preferred embodiments the device includes a plurality of acoustic transducers.

According to still further features in the described preferred embodiments each of the plurality of acoustic transducers generates an electrical signal which leads to permeabilization of a barrier of a corresponding reservoir of the plurality of reservoirs.

According to still further features in the described preferred embodiments each of the plurality of acoustic transducers is capable of converting an acoustic signal of a distinct frequency or frequencies into the electrical signal.

According to still further features in the described preferred embodiments the plurality of reservoirs are for containing different types of molecules, different amounts of molecules, or combinations thereof.

According to still further features in the described preferred embodiments the molecules are drug molecules.

According to still further features in the described preferred embodiments the at least one acoustic transducer includes: (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

According to still further features in the described preferred embodiments the device includes a plurality of reservoirs each containing molecules of a specific type and each capable of releasing the molecules upon provision of an acoustic signal of a specific frequency or frequencies, such that a frequency content of the acoustic signal determines a type of the molecules released.

According to an additional aspect of the present invention there is provided a device for controlled drug release comprising: (a) a device body including at least one reservoir being for containing a prodrug form of a drug, the at least one reservoir being formed with a barrier impermeable to the prodrug thereby preventing release thereof from the at least one reservoir; and (b) at least one acoustic transducer being attached to, or forming a part of the device body, the at least one acoustic transducer being for converting an acoustic signal received thereby into an electrical signal, the electrical signal leading to a conversion of the prodrug into the drug, the drug being capable of traversing the barrier thereby releasing from the at least one reservoir.

According to yet an additional aspect of the present invention there is provided a system for localized delivery of molecules within the body comprising: (a) an intrabody implantable device including: (i) a device body including at least one reservoir being for containing a prodrug form of a drug, the at least one reservoir being formed with a barrier impermeable to the prodrug thereby preventing release thereof from the at least one reservoir; and (ii) at least one acoustic transducer being attached to, or forming a part of the device body, the at least one acoustic transducer being for converting an acoustic signal received thereby into an electrical signal, the electrical signal leading to a conversion of the prodrug into the drug, the drug being capable of traversing the barrier thereby releasing from the at least one reservoir; and (b) an extracorporeal unit for generating the acoustic signal.

According to still further features in the described preferred embodiments a type or duration of the electrical signal controls a degree of the conversion and thus an amount of the drug formed and released.

According to still further features in the described preferred embodiments the device includes a plurality of reservoirs and a plurality of acoustic transducers, each of the plurality of acoustic transducers generating an electrical signal which leads to the conversion of the prodrug to the drug contained in a corresponding reservoir of the plurality of reservoirs.

According to still further features in the described preferred embodiments the plurality of reservoirs are for containing different types of prodrugs, different amounts of prodrugs, or combinations thereof.

According to still an additional aspect of the present invention there is provided a method of fabricating a device for controllable release of molecules, the method comprising: (a) providing a substrate; (b) configuring the substrate with the at least one reservoir; (c) capping the at least one reservoir with a cap material which acts as an impermeable barrier to the molecules, the material becoming permeable to the molecules following generation of an electrical potential in or around the at least one reservoir; and (d) providing an inlet port for filling the at least one reservoir with the molecules, the inlet being sealable following the filling, thereby generating the device for controllable release of molecules.

According to still further features in the described preferred embodiments the method further comprising the step of: (e) attaching to, or fabricating within, the substrate, at least one acoustic transducer, the at least one acoustic transducer being for generating an electrical signal from an acoustic signal received thereby, the electrical signal leading to generation of the electrical potential in or around the at least one reservoir.

According to still further features in the described preferred embodiments the at least one acoustic transducer includes: (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

According to still further features in the described preferred embodiments step (b) is effected by etching the substrate.

The present invention successfully addresses the shortcomings of the presently known configurations by providing a device, system and method for efficient intrabody delivery of molecules such as drugs as well as a method of manufacture.

The present invention also relates to a miniature flexural transducer element, comprising, (a) a cell element having a cavity; (b) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (c) a first electrode attached to the external surface and a second electrode attached to the internal surface of the piezoelectric layer. Preferably, the cavity is etched into a substrate including an electrically insulating layer and an electrically conducting layer. The first electrode is preferably integrally made with a substantially thin electrically conducting layer, the electrically conducting layer being disposed on the substrate and connected thereto by a sealing connection. The cell member may be circular or hexagonal in cross section. According to further features in preferred embodiments of the invention described below, the substrate may include a plurality of cell members electrically connected in parallel or serial connections. Preferably, at least one of the electrodes is specifically shaped so as to provide a maximal electrical output, wherein the electrical output may be current, voltage or power. A preferred shape of the electrodes includes two cores interconnected by a connecting member. A transducer element according to the present invention may also be used as a transmitter.

Preferably, the cavity of the transducer element includes gas of low pressure so as to allow its usage as a transmitter. According to the present invention there is further provided a transmitter element, comprising: (a) a cell element having a cavity; (b) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (c) a first electrode attached to the external surface and a second electrode attached to the internal surface of the piezoelectric layer, the electrodes being electrically connected to an electrical circuit including a switching element for controllably changing the mechanical impedance of the piezoelectric layer. Preferably, the switching frequency of the switching element equals the frequency of an electrical message signal arriving from an electronic member, such as a sensor, thereby modulating a reflected acoustic wave according to the frequency of the message signal. The transmitter element may include a third electrode attached to the external surface and a fourth electrode attached to the internal surface of the piezoelectric layer. When using such a configuration, the switching element preferably alternately connects the electrodes in parallel and anti-parallel, thereby controllably changing the mechanical impedance of the piezoelectric layer. According to a specific configuration, the electrodes are interconnected by means of a built-in anti-parallel electrical connection. Alternatively, the electrodes may be interconnected by means of a built-in parallel electrical connection. The switching element may be an on/off switch. According to another embodiment, the piezoelectric layer includes first and second portions having opposite polarities. According to yet another embodiment, the transmitter element may include two cell members electrically interconnected by means of a built-in parallel or anti-parallel electrical connection. Alternatively, the switching element may alternately connect the cell members in parallel and anti-parallel electrical connections. The cell members may have piezoelectric layers of opposite polarities. According to yet another embodiment the cavity of the transmitter element is covered by a two-ply piezoelectric layer including an upper layer bonded to a lower layer. The upper and lower layers may feature opposite polarities. The upper and lower layers may be separated by an insulating layer disposed therebetween.

Further according to the present invention there is provided a method of transmitting acoustic information, comprising: (a) providing a substantially flexible piezoelectric layer having first and second electrodes attached thereto, the piezoelectric layer being attached to a cell member, the electrodes being electrically connected to an electrical circuit including a switching element; (b) providing an acoustic wave for impinging on the piezoelectric layer, the acoustic wave having a reflected portion; (c) modulating the reflected portion of the acoustic wave by controlling the mechanical impedance of the piezoelectric layer, said controlling by switching the switching element at a frequency which equals the frequency of a message signal arriving from an electronic component such as a sensor. The method may further comprise: (a) providing third and fourth electrodes attached to the piezoelectric layer, the third and fourth electrodes being electrically connected to the electrical circuit; (b) changing the electrical connections between the electrodes by means of the switching element so as to change the mechanical impedance of the piezoelectric layer. According to a specific configuration, the first and second electrodes are attached to a first cell member and the third and fourth electrodes are attached to a second cell member.

The present invention successfully addresses the shortcomings of the presently known configurations by providing a miniature flexural piezoelectric transducer specifically tailored so as to allow the usage of low frequency acoustic signals for vibrating the piezoelectric layer at its resonant frequency, wherein substantially low frequency signals herein refer to signals having a wavelength that is much larger than dimensions of the transducer. Further, the present invention addresses the shortcomings of the presently known configurations by providing such transducer element having electrodes specifically shaped so as to maximize the electrical output of the transducer, and which may be integrally manufactured with any combination of electronic circuits by using photolithographic and microelectronics technologies.

Further, the present invention addresses the shortcomings of the presently known configurations by providing a miniature flexural piezoelectric transmitter which modulates a reflected acoustic wave by controllably changing the mechanical impedance of the piezoelectric layer according to a message signal received from an electronic component such as a sensor. Further, the present invention addresses the shortcomings of the presently known configurations by providing such transmitter wherein the mechanical impedance of the piezoelectric layer is controlled by providing a plurality of electrodes attached thereto, the electrodes being interconnected in parallel and anti-parallel electrical connections, and wherein at least a portion of the electrodes is electrically connected to a switching element, the switching element for alternately changing the electrical connections between the electrodes so as to alternately change the mechanical impedance of the piezoelectric layer.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 3a is a cross section of a transducer element according to the present invention taken along line C-C in FIG. 2a;

FIG. 3b is a cross section of a transducer element according to the present invention taken along line D-D in FIG. 2a;

FIG. 3c is a cross section of a transducer element according to the present invention taken along line E-E in FIG. 2a;

FIG. 3d is a cross section of a transducer element according to the present invention taken along line F-F in FIG. 2a;

FIG. 3e is a cross section of a transducer element according to the present invention taken along line G-G in FIG. 2a;

FIG. 8a-8f are schematic views of possible configurations of transmitters according to the present invention including parallel and anti-parallel electrical connections for controllably changing the mechanical impedance of the piezoelectric layer;

DESCRIPTION OF THE PREFERRED EMBODIMENTS

Figure 1:
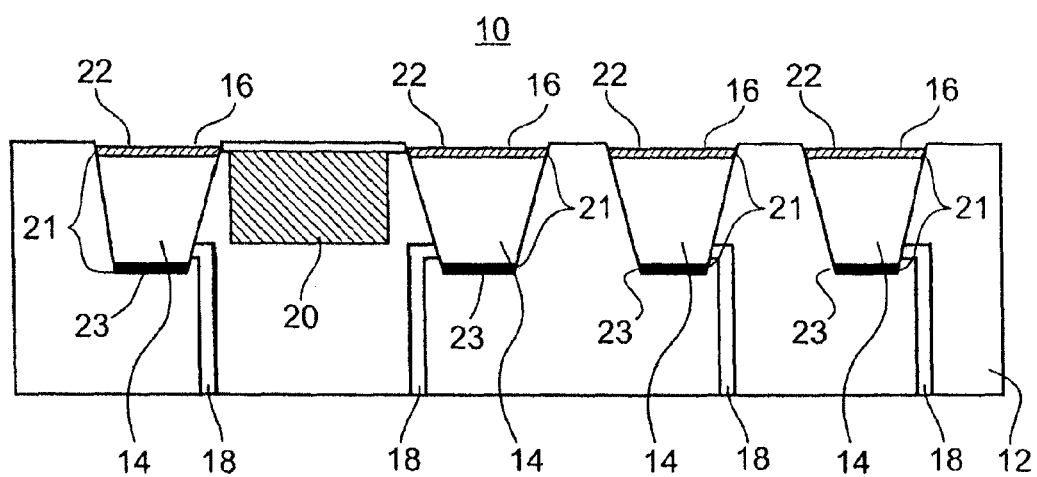
FIG. 1 is a cross sectional view of a general configuration of the device of the present invention.

The present invention is of a device, system, and method which can be used for localized intrabody delivery of molecules. Specifically, the present invention can be used to release molecules such as drugs within a specific body region using an acoustic activation signal provided from outside the body.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a device for controlled release of molecules, which is referred to herein as device 10.

Device 10 includes a device body 12 having at least one reservoir 14 formed therein for containing the molecules to be delivered.

Preferably, device body 12 includes a plurality of reservoirs 14 (four shown in FIG. 1) each being configured for containing therapeutic molecules such as drugs and/or diagnostic molecules such as dyes preferably in a solution or as a suspension. Reservoirs 14 can be of various dimensions depending on the molecule type and quantity to be delivered therefrom.

Device body 12 can be of a planar shape; spheroidal shape or any shape suitable for intrabody implantation and delivery of molecules stored thereby. Reservoirs 14 can be formed within a surface of device body 12 or within an interior volume thereof, provided molecules released therefrom can disperse into a medium surrounding device 10.

The dimensions of device 10 are limited by the site of implantation and delivery, the quantity of drugs or drugs to be delivered thereby, and the specific components used thereby for drug release activation.

Reservoirs 14 can be formed within device body 12 using any method known in the art including, but not limited to, etching, machining and the like. Alternatively, device body 12 may be pre-formed with reservoirs 14 by, for example, casting or milling techniques.

Device body 12 is fabricated from a material which is impermeable to the molecules to be delivered and to the surrounding fluids, for example, water, blood, electrolytes or other solutions. Examples of suitable materials include ceramics, semiconductors, biological membranes, and degradable and non-degradable polymers; biocompatibility is preferred, but not required.

For in-vivo applications, non-biocompatible materials may be encapsulated in a biocompatible material, such as polyethyleneglycol or polytetrafluoroethylene-like materials, before use. One example of a strong, non-degradable, easily etched substrate that is impermeable to the molecules to be delivered and the surrounding fluids is silicon.

Alternatively, device body 12 can also be fabricated from a material which degrades or dissolves over a period of time into biocompatible components such as Polyvinyl Alcohol (PVA). This embodiment is preferred for in vivo applications where the device is implanted and physical removal of the device at a later time is not feasible or recommended, as is the case with, for example, brain implants. An example of a class of strong, biocompatible materials are the poly(anhydride-co-imides) discussed by K. E. Uhrich et al., "Synthesis and characterization of degradable poly(anhydride-co-imides)", Macromolecules, 1995, 28, 2184-93.

Reservoir 14 is formed (capped) with a barrier 16 which is impermeable to the molecules to be delivered. As such barrier 16 serves for preventing molecules contained within reservoir 14 from releasing into the surrounding medium when device 10 is implanted within the body.

Reservoir 14 can be filled with molecules of interest either prior to capping with barrier 16 or following such capping. In the latter case, reservoir 14 also includes an inlet port 18, which serves for filling reservoir 14 with molecules of choice following fabrication of device 10. Inlet port 18 is designed to be sealable following filling, such that accidental drug release therefrom does not occur.

Device 10 further includes at least one acoustic transducer 20. Acoustic transducer 20 can be attached to, or it can form a part of, device body 12. Acoustic transducer 20 serves for converting an acoustic signal received thereby into an electrical signal. The electrical signal generated by transducer 20 is preferably rectified via a full or half-bridge rectifier into a DC current signal. The converted electrical signal can be used to directly or indirectly release the molecules stored in reservoir 14 as described hereinbelow.

According to a preferred embodiment of the present invention, the electrical signal generates (directly or indirectly) an electrical potential within reservoir 14.

To this end, device 10 further includes at least one pair of electrodes 21, which are preferably positioned within reservoir 14 and which serve for providing the electrical potential therein.

According to one preferred embodiment of the present invention, the electrical potential converts the molecules stored within reservoir 14 into an active and barrier permeable form.

For example, the molecules contained within reservoir 14 can be provided as large aggregates which are unable to traverse barrier 16 which can be, in this case, a size selective membrane. Upon provision of the electrical potential the molecules disaggregate into smaller active units which are able to diffuse out of reservoir 14 through barrier 16.

According to another preferred embodiment of the present invention, the electrical potential leads to permeabilization of barrier 16 and subsequent release of the molecules from reservoir 14.

For example, the electrical potential generated by electrodes 21 can cause the partial or full disintegration of barrier 16 and as such the release of the molecules from reservoir 14.

In such a case, barrier 16 can be composed of a thin film of conductive material that is deposited over the reservoir, patterned to a desired geometry, and functions as an anode 22. The size and placement of cathode 23 depends upon the device's application and method of electric potential control.

Conductive materials capable of dissolving into solution or forming soluble compounds or ions upon the application of an electric potential, include, but are not limited to, metals such as copper, gold, silver, and zinc and some polymers.

Thus, according to this configuration of device 10, when an electric potential is applied between anode 22 and cathode 23, the conductive material of the anode above the reservoir oxidizes to form soluble compounds or ions that dissolve into solution, exposing the molecules to be delivered to the surrounding medium.

Alternatively, the application of an electric potential can be used to create changes in local pH near barrier 16 thereby leading to dissolving of barrier 16 and release of the molecules.

Still alternatively, the application of an electric potential can be used to create changes in the net charge of barrier 16 or the net charge or solubility of the molecules thereby enabling barrier 16 traversing.

In any case, the molecules to be delivered are released into the surrounding medium by diffusion out of or by degradation or dissolution of the release system. The frequency and quantity of release can be controlled via the acoustic signal received by acoustic transducer 20 as is further described hereinbelow.

FIGS. 2a, 2b and 3a-3e illustrate a preferred embodiment of a transducer element according to the present invention. As shown in the figures, the transducer element 20 includes at least one cell member 25 including a cavity 24 etched or drilled into a substrate and covered by a substantially flexible piezoelectric layer 26. Attached to piezoelectric layer 26 are an upper electrode 28 and a lower electrode 30 which are connectable to an electronic circuit. The substrate is preferably made of an electrical conducting layer 32 disposed on an electrically insulating layer 34, such that cavity 24 is etched substantially through the thickness of electrically conducting layer 32.

Electrically conducting layer 32 is preferably made of copper and insulating layer 34 is preferably made of a polymer such as polyimide. Conventional copper-plated polymer laminate such as KAPTON sheets may be used for the production of transducer 20. Commercially available laminates such as NOVOCLAD may be used. Alternatively, the substrate may include a silicon layer, or any other suitable material. Alternatively, layer 32 is made of a non-conductive material such as PYRALIN.

Preferably, cavity 24 is etched into the substrate by using conventional printed-circuit photolithography methods. Alternatively, cavity 24 may be etched into the substrate by using VLSI/micro-machining technology or any other suitable technology.

Piezoelectric layer 26 may be made of PVDF or a copolymer thereof. Alternatively, piezoelectric layer 26 is made of a substantially flexible piezoceramic. Preferably, piezoelectric layer 26 is a poled PVDF sheet having a thickness of about 9-28 μm.

Preferably, the thickness and radius of flexible layer 26, as well as the pressure within cavity 24, are specifically selected so as to provide a predetermined resonant frequency. When using the embodiment of FIGS. 2a and 2b, the radius of layer 26 is defined by the radius of cavity 24.

By using a substantially flexible piezoelectric layer 26, the present invention allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The present invention provides a transducer which is omni-directional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

The configuration and acoustic properties of such an acoustic transducer and variants thereof as well as general acoustic transduction principles are described in detail in U.S. Pat. No. 6,140,740 and PCT Publication No. WO 99/34,453 the disclosures of which are expressly incorporated by reference as if fully set forth herein.

According to a specific embodiment, cavity 24 features a circular or hexagonal shape with radius of about 200 μm. Electrically conducting layer 32 preferably has a thickness of about 15 μm. Cell member 25 is preferably etched completely through the thickness of electrically conducting layer 32.

Electrically insulating layer 34 preferably features a thickness of about 50 μm. The precise dimensions of the various elements of a transducer element according to the present invention may be specifically tailored according to the requirements of the specific application.

Cavity 24 preferably includes a gas such as air. The pressure of gas within cavity 24 may be specifically selected so as to predetermine the sensitivity and ruggedness of the transducer as well as the resonant frequency of layer 26.

Figure 3A:
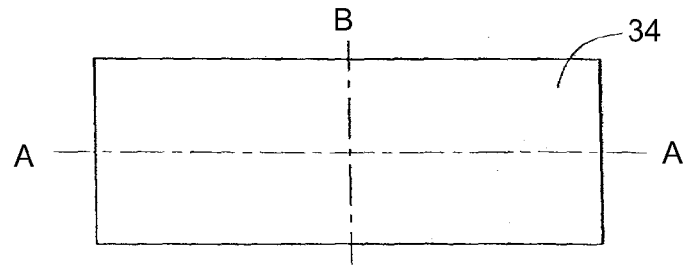
Figure 3B:
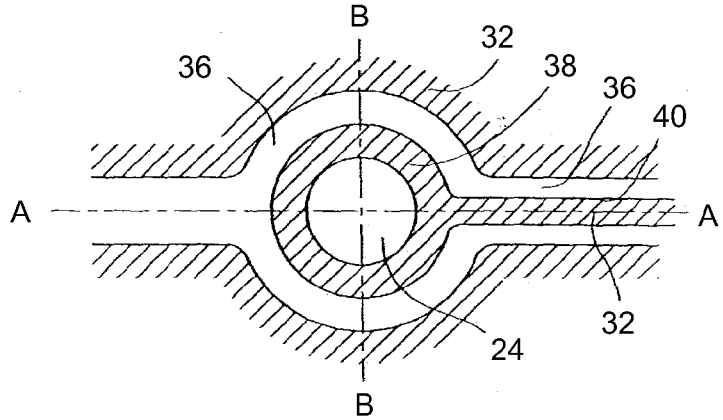

As shown in FIG. 3b, an insulating chamber 36 is etched into the substrate, preferably through the thickness of conducting layer 32, so as to insulate the transducer element from other portions of the substrate which may include other electrical components such as other transducer elements etched into the substrate. According to a specific embodiment, the width of insulating chamber 36 is about 100 μm. As shown, insulating chamber 36 is etched into the substrate so as to form a wall 38 of a predetermined thickness enclosing cavity 24, and a conducting line 40 integrally made with wall 38 for connecting the transducer element to another electronic component preferably etched into the same substrate, or to an external electronic circuit.

Figure 2A:
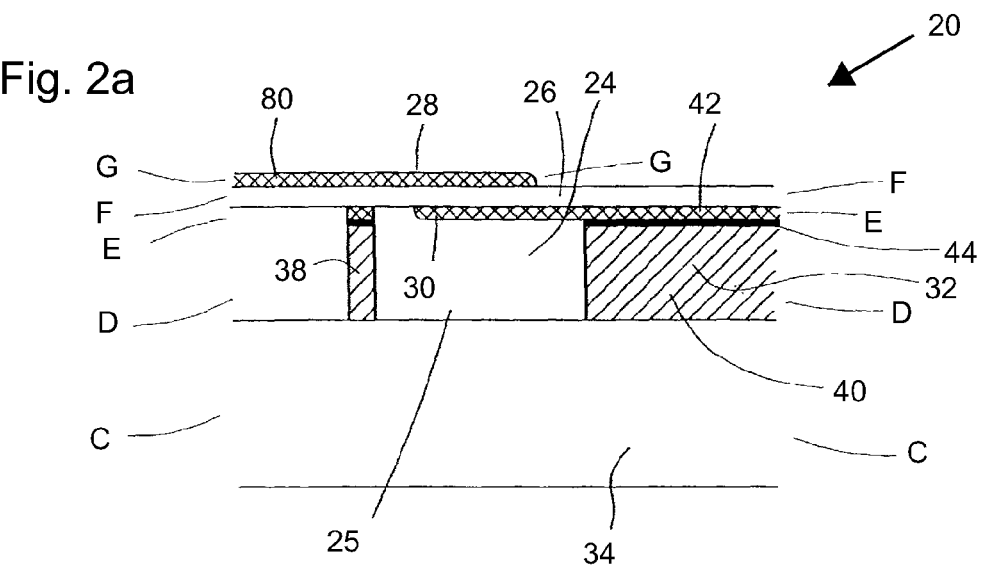
FIG. 2a is a longitudinal section of a transducer element according to the present invention taken along lines A-A in FIGS. 3a-3e.
Figure 2B:
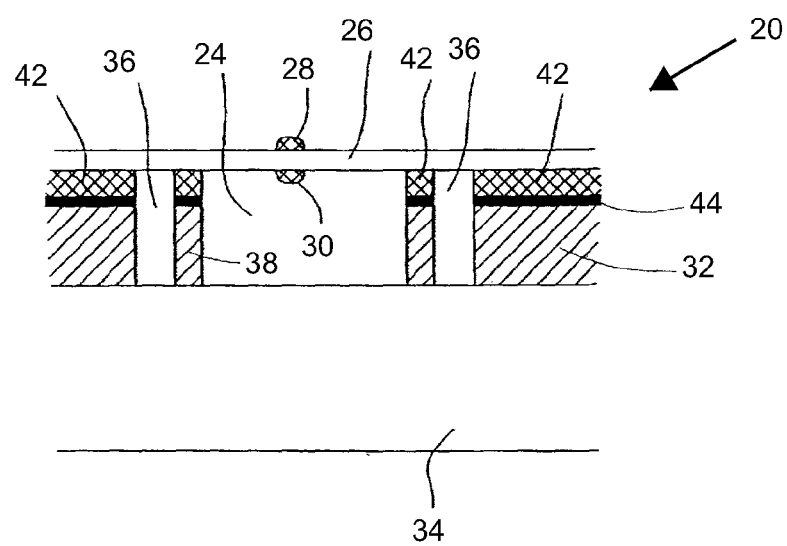
FIG. 2b is a longitudinal section of a transducer element according to the present invention taken along lines B-B in FIGS. 3a-3e.
Figure 3C:
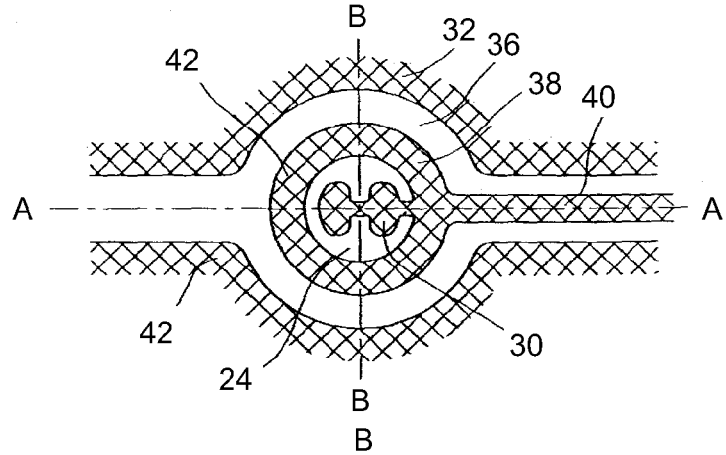
Figure 3D:
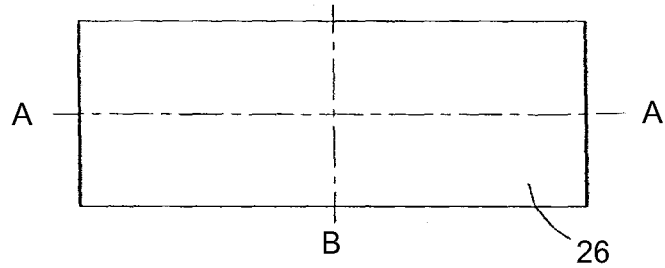
Figure 3E:
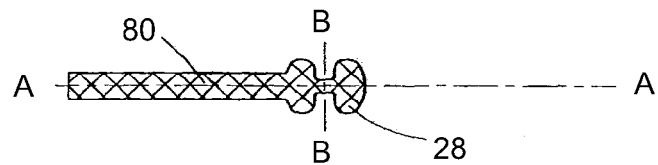

As shown in FIGS. 2a and 2b, attached to piezoelectric layer 26 are upper electrode 28 and lower electrode 30. As shown in FIGS. 3c and 3e, upper electrode 28 and lower electrode 30 are preferably precisely shaped so as to cover a predetermined area of piezoelectric layer 26. Electrodes 28 and 30 may be deposited on the upper and lower surfaces of piezoelectric membrane 26, respectively, by using various methods such as vacuum deposition, mask etching, painting, and the like.

As shown in FIG. 2a, lower electrode 30 is preferably made as an integral part of a substantially thin electrically conducting layer 42 disposed on electrically conducting layer 32. Preferably, electrically conducting layer 42 is made of a Nickel-Copper alloy and is attached to electrically conducting layer 32 by means of a sealing connection 44. Sealing connection 44 may be made of indium. According to a preferred configuration, sealing connection 44 may feature a thickness of about 10 μm, such that the overall height of wall 38 of cavity 24 is about 20-25 μm.

As shown in FIG. 3c, electrically conducting layer 42 covers the various portions of conducting layer 32, including wall 38 and conducting line 40. The portion of conducting layer 42 covering conducting line 40 is for connection to an electronic component such as a neighboring cell.

According to a preferred embodiment of the present invention, electrodes 28 and 30 are specifically shaped to include the most energy-productive region of piezoelectric layer 26 so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 26, ψ, resulting from a monochromatic excitation at angular frequency ω is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 26; h the half-thickness of layer 26; v is the Poisson ratio for layer 26; $\gamma$ is the effective wavenumber in the layer given by: $\gamma^4 = 3\rho(1-v^2)\omega^2/Qh^2$, wherein $\rho$ is the density of layer 26 and $\omega$ is the angular frequency of the applied pressure (wherein the applied pressure may include the acoustic pressure, the static pressure differential across layer 26 and any other pressure the transducer comes across); Z is the mechanical impedance resulting from the coupling of layer 26 to both external and internal media of cavity 24, wherein the internal medium is preferably air and the external medium is preferably fluid; P is the acoustic pressure applied to layer 26, and $\Psi$ represents the average vertical displacement of layer 26.

When chamber 24 is circular, the solution (given for a single frequency component $\omega$) representing the dynamic displacement of a circular layer 26 having a predetermined radius a, expressed in polar coordinates, is:

$$\Psi(r,\varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \quad L_2(z) = J_2(z)I_1(z) - I_2(z)J_1(z)$$

$$Z = \frac{P_A}{i\omega H_A} + i\left[\frac{4}{3\pi} + \frac{1}{6}\right]\varphi\rho_W a$$

wherein:

$\psi(r,\phi)$ is time-dependent and represents the displacement of a selected point located on circular layer 26, the specific location of which is given by radius r and angle $\omega$);

J and I are the normal and modified Bessel functions of the first kind, respectively;

$P_A$, $H_A$ are the air pressure within cavity 24 and the height of chamber 24, respectively; and $\rho_W$ is the density of the fluid external to cavity 24.

The first term of the impedance Z relates to the stiffness resulting from compression of air within cavity 24, and the second term of Z relates to the mass added by the fluid boundary layer. An additional term of the impedance Z relating to the radiated acoustic energy is substantially negligible in this example.

The charge collected between electrodes 28 and 30 per unit area is obtained by evaluating the strains in layer 26 resulting from the displacements, and multiplying by the pertinent off-diagonal elements of the piezoelectric strain coefficient tensor, $e_{31}$, $e_{32}$, as follows:

$$Q(r,\varphi,t) = \left(e_{31}\left(\frac{\partial \Psi}{\partial x}\right)\right)^2 + \left(e_{32}\left(\frac{\partial \Psi}{\partial y}\right)\right)^2$$

wherein:

$Q(r,\phi,t)$ represents the charge density at a selected point located on circular layer 26, the specific location of which is given by radius r and angle $\phi$;

x is the stretch direction of piezoelectric layer 26;

y is the transverse direction (the direction perpendicular to the stretch direction) of layer 26;

$e_{31}$, $e_{32}$ are off-diagonal elements of the piezoelectric strain coefficient tensor representing the charge accumulated at a selected point on layer 26 due to a given strain along the x and y directions, respectively, which coefficients being substantially dissimilar when using a PVDF layer; and $\psi$ is the displacement of layer 26, taken as the sum of the displacement for a given acoustic pressure P at frequency f, and the static displacement resulting from the pressure differential between the interior and exterior of cavity 24, which displacements being extractable from the equations given above.

The total charge accumulated between electrodes 28 and 30 is obtained by integrating $Q(r,\phi,t)$ over the entire area S of the electrode:

$$Q = \int_S Q(r,\phi,t)d\bar{x}$$

The capacitance C of piezoelectric layer 26 is given by:

$$C = \frac{\varepsilon}{2h}\int_S d\bar{x},$$

wherein $\varepsilon$ is the dielectric constant of piezoelectric layer 26; and $2h$ is the thickness of piezoelectric layer 26.

Accordingly, the voltage, current and power responses of piezoelectric layer 26 are evaluated as follows:

$$V = \frac{2h\int_N Q(r,\varphi,t)d\bar{x}}{\varepsilon \int_N d\bar{x}},$$

$$I = 2i\omega \int_S Q(r,\varphi,t)d\bar{x},$$

$$W = \frac{4ih\left[\int_S Q(r,\varphi,t)d\bar{x}\right]^2}{\varepsilon \int_S d\bar{x}}$$

The DC components of Q are usually removed prior to the evaluation, since the DC currents are usually filtered out. The values of Q given above represent peak values of the AC components of Q, and should be modified accordingly so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 4:
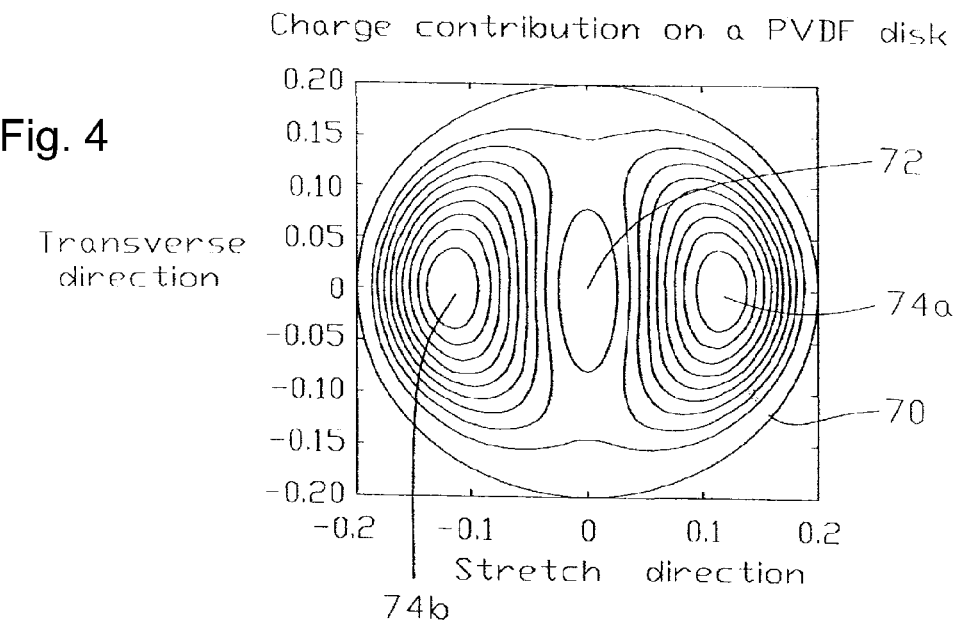
FIG. 4 shows the distribution of charge density across a piezoelectric layer of a transducer element resulting from the application of a constant pressure over the entire surface of the layer.

FIG. 4 shows the distribution of charge density on a circular piezoelectric layer 26 obtained as a result of pressure (acoustic and hydrostatic) applied uniformly over the entire area of layer 26, wherein specific locations on layer 26 are herein defined by using Cartesian coordinates including the stretch direction (x direction) and the transverse direction (y direction) of layer 26. It can be seen that distinct locations on layer 26 contribute differently to the charge density. The charge density vanishes at the external periphery 70 and at the center 72 of layer 26 due to minimal deformation of these portions. The charge density is maximal at two cores 74a and 74b located symmetrically on each side of center 72 due to maximal strains (in the stretch direction) of these portions.

A preferred strategy for optimizing the electric responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 26.

Figure 5A:
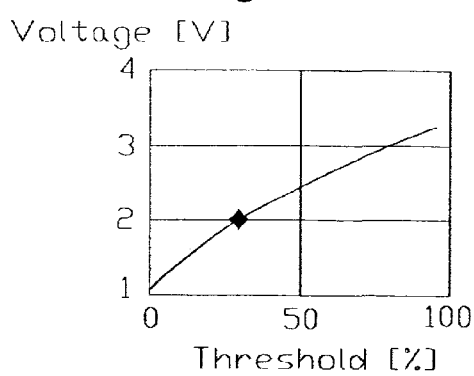
FIGS. 5a-5d show the results of optimization performed for the power response of a transducer according to the present invention.
Figure 5C:
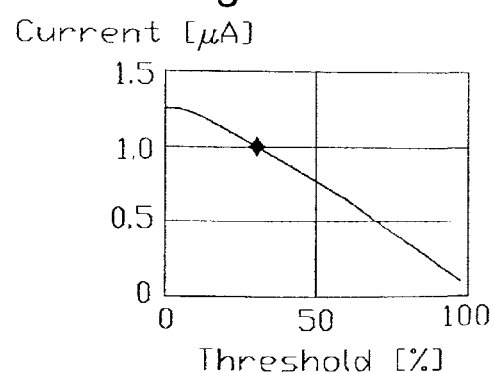
Figure 5B:
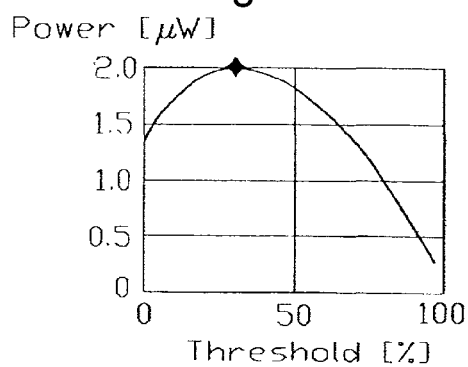
Figure 5D:
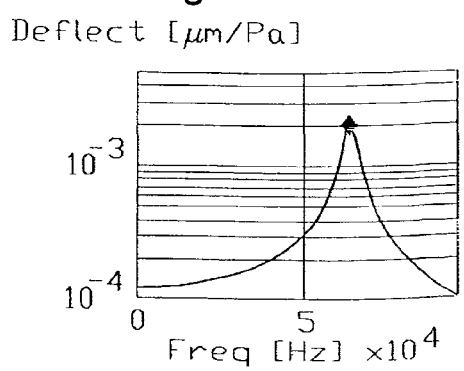

FIGS. 5a-5d show the results of an optimization performed for the power response of a transducer having a layer 26 of a predetermined area. As shown in the figures, the threshold value which provides an optimal power response is about 30% (FIG. 5b). Accordingly, an electrode which covers only the portions of layer 26 contributing at least 30% of the maximal charge density yields a maximal power response. The pertinent voltage response obtained by such an electrode is higher by a factor of 2 relative to an electrode completely covering layer 26 (FIG. 5a). The current response obtained by such electrode is slightly lower relative to an electrode completely covering layer 26 (FIG. 5c). Further as shown in the figures, the deflection of layer 26 is maximal when applying an acoustic signal at the resonant frequency of layer 26 (FIG. 5d).

Figure 6:
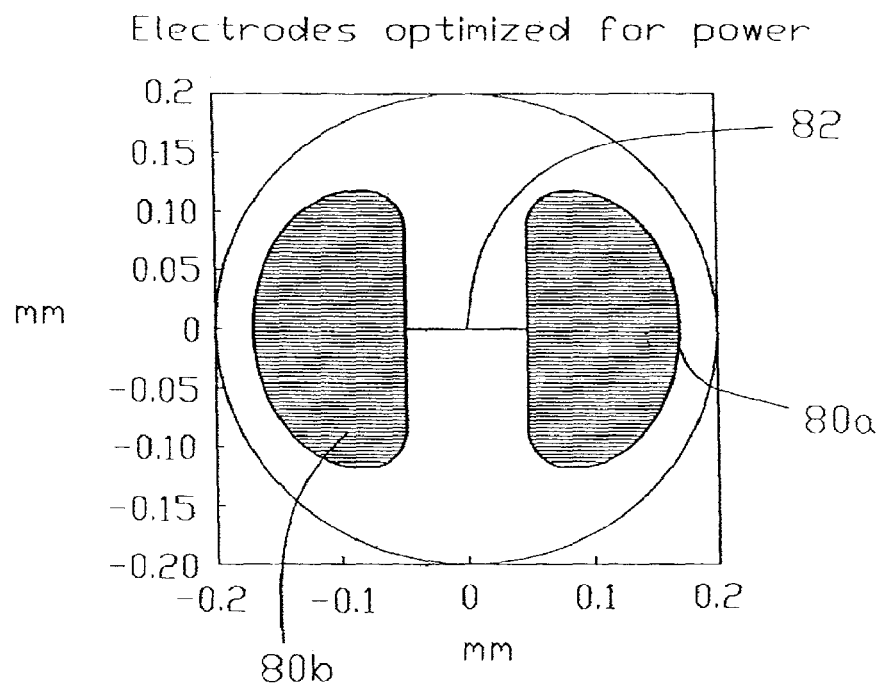
FIG. 6 shows a preferred electrode shape for maximizing the power response of a transducer according to the present invention.

A preferred electrode shape for maximizing the power response of the transducer is shown in FIG. 6, wherein the electrode includes two electrode portions 80a and 80b substantially covering the maximal charge density portions of layer 26, the electrode portions being interconnected by means of a connecting member 82 having a minimal area. Preferably, portions 80a and 80b cover the portions of layer 26 which yield at least a selected threshold (e.g. 30%) of the maximal charge density.

According to the present invention any other parameter may be optimized so as to determine the shape of electrodes 28 and 30. According to further features of the present invention, only one electrode (upper electrode 28 or lower electrode 30) may be shaped so as to provide maximal electrical response of the transducer, with the other electrode covering the entire area of layer 26. Since the charge is collected only at the portions of layer 26 received between upper electrode 28 and lower electrode 30, such configuration is operatively equivalent to a configuration including two shaped electrodes having identical shapes.

Figure 7:
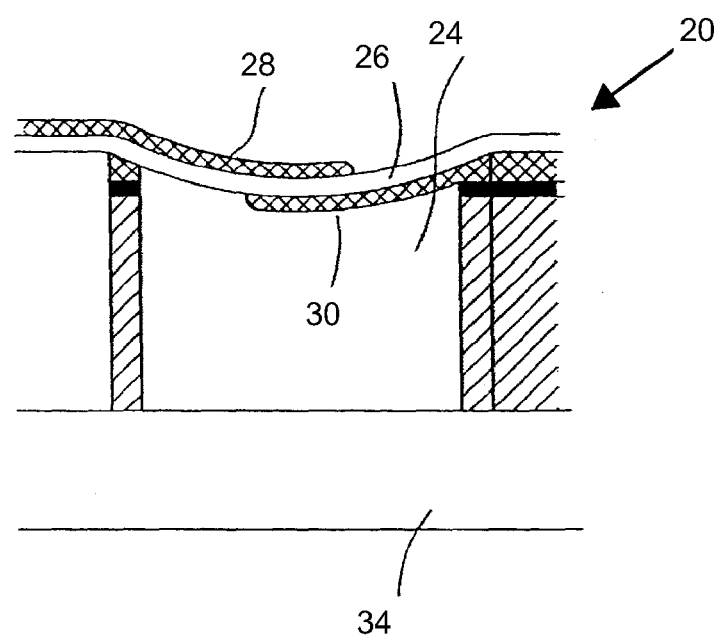
FIG. 7 is a longitudinal section of another embodiment of a transducer element according to the present invention capable of functioning as a transmitter.

Referring now to FIG. 7, according to another embodiment of the present invention chamber 24 of transducer element 20 may contain gas of substantially low pressure, thereby conferring a substantially concave shape to piezoelectric membrane 26 at equilibrium. Such configuration enables to further increase the electrical response of the transducer by increasing the total charge obtained for a given displacement of layer 26. The total displacement in such an embodiment is given by: $\psi = P_0 \psi_{DC} + P \psi_{AC} \cos \omega t$, wherein $P_0$ is the static pressure differential between the exterior and the interior of cavity 24; $\psi_{DC}$ is the displacement resulting from $P_0$; P is the amplitude of the acoustic pressure; and $\psi_{DC}$ the displacement resulting from P.

Accordingly, the strain along the x direction includes three terms as follows:

$$S_{xx} = \left(\frac{\partial \Psi}{\partial x}\right)^2$$
$$= \left(P_0^2 \left(\frac{\partial \Psi_{DC}}{\partial x}\right)\right)^2 + \left(P^2 \left(\frac{\partial \Psi_{AC}}{\partial x}\right)\right)^2 \cos^2 \omega t +$$
$$2 P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium (preferably air) within cavity 24 relative to the pressure of the external medium (preferably fluid), the value of $P_0$ is increased, thereby increasing the value of the third term of the above equation.

Such embodiment of the present invention makes it possible to increase the charge output of layer 26 for a given displacement, thereby increasing the voltage, current and power responses of the transducer without having to increase the acoustic pressure P. Further, such embodiment enables to further miniaturize the transducer since the same electrical response may obtain for smaller acoustic deflections. Such embodiment is substantially more robust mechanically and therefore more durable than the embodiment shown in FIGS. 2a and 2b. Such further miniaturization of the transducer enables to use higher resonance frequencies relative to the embodiment shown in FIGS. 2a and 2b.

Preferably, a transducer element 20 according to the present invention is fabricated by using technologies which are in wide use in the microelectronics industry so as to allow integration thereof with other conventional electronic components. When the transducer element includes a substrate such as Copper-polymer laminate or silicon, a variety of conventional electronic components may be fabricated onto the same substrate.

According to the present invention, a plurality of cavities 24 may be etched into a single substrate 34 and covered by a single piezoelectric layer 26 so as to provide a transducer element including a matrix of transducing cells members 25, thereby providing a larger energy collecting area of predetermined dimensions while still retaining the advantage of miniature individual transducing cell members 25. When using such configuration, the transducing cell members 25 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Further, piezoelectric layer 26 may be completely depolarized and then repolarized at specific regions thereof so as to provide a predetermined polarity to each of the transducing cell members 25. Such configuration reduces the complexity of interconnections between the cell members 25.

A transducer element according to the present invention may be further used as a transmitter for transmitting information to a remote receiver by modulating the reflection of an external impinging acoustic wave arrived from a remote transmitter Referring to FIG. 7, the transducer element shown may function as a transmitter element due to the asymmetric fluctuations of piezoelectric layer 26 with respect to positive and negative transient acoustic pressures obtained as a result of the pressure differential between the interior and exterior of cavity 24.

A transmitter element according to the present invention preferably modulates the reflection of an external impinging acoustic wave by means of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 26 according to the frequency of the message signal.

Preferably, the invention uses a specific array of electrodes connected to a single cell member 25 or alternatively to a plurality of cell members 25 so as to control the mechanical impedance of layer 26.

Figure 8D:
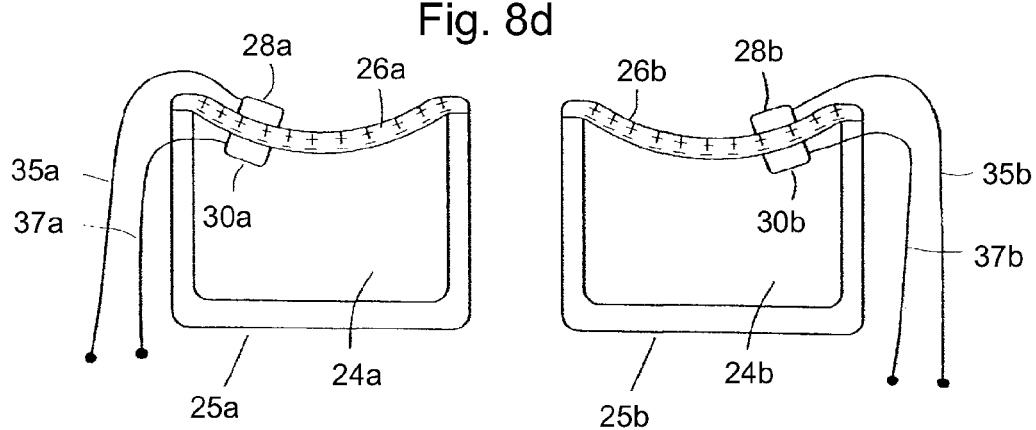

FIGS. 8a-8g illustrate possible configurations for controllably changing the impedance of layer 26 of a transmitter element. Referring to FIG. 8a, a transmitter element according to the present invention may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by means of conducting lines 36a, 36b, 34a and 34b, respectively, the electrical circuit including a switching element (not shown) so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 26, wherein an anti-parallel connection increases the mechanical impedance of layer 26. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor.

According to another embodiment (FIG. 8b), upper electrode 40a is connected to lower electrode 38b by means of a conducting line 60, and electrodes 38a and 40b are connected to an electrical circuit by means of conducting lines 62 and 64, respectively, the electrical circuit including a switching element. Such configuration provides an anti-parallel connection of the electrodes, wherein the switching element functions as an on/off switch, thereby alternately increasing the mechanical impedance of layer 26.

In order to reduce the complexity of the electrical connections, layer 26 may be depolarized and then repolarized at specific regions thereof. As shown in FIG. 8c, the polarity of the portion of layer 26 received between electrodes 40a and 38a is opposite to the polarity of the portion of layer 26 received between electrodes 40b and 38b. An anti-parallel connection is thus achieved by interconnecting electrodes 38a and 38b by means of a conducting line 60, and providing conducting lines 62 and 64 connected to electrodes 40a and 40b, respectively, the conducting lines for connection to an electrical circuit including a switching element.

According to another embodiment, the transmitting element includes a plurality of transducing cell members, such that the mechanical impedance of layer 26 is controllably changed by appropriately interconnecting the cell members.

As shown in FIG. 8d, a first transducing cell member 25a including a layer 26a and a cavity 24a, and a second transducing cell member 25b including a layer 26b and a cavity 24b are preferably contained within the same substrate; and layers 26a and 26b are preferably integrally made (not shown). A first pair of electrodes including electrodes 28a and 30a is attached to layer 26, and a second pair of electrodes including electrodes 28b and 30b is attached to layer 26b. Electrodes 28a, 30a, 28b and 30b are electrically connected to an electrical circuit by means of conducting lines 37a, 35a, 37b and 35b, respectively, the electrical circuit including a switching element so as to alternately switch the electrical connections of conducting lines 37a, 35a, 37b and 35b so as to alternately provide parallel and anti-parallel connections, substantially as described for FIG. 8a, thereby alternately decreasing and increasing the mechanical impedance of layers 26a and 26b.

Figure 8E:
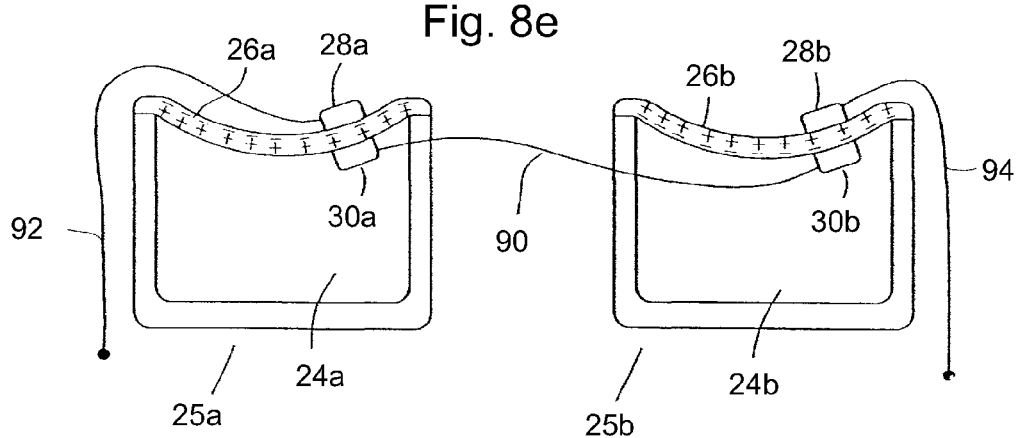

FIG. 8e illustrates another embodiment, wherein the first and second transducing cell members are interconnected by means of an anti-parallel connection. As shown in the figure, the polarity of layer 26a is opposite to the polarity of layer 26b so as to reduce the complexity of the electrical connections between cell members 25a and 25b. Thus, electrode 30a is connected to electrode 30b by means of a conducting line 90, and electrodes 28a and 28b are provided with conducting lines 92 and 94, respectively, for connection to an electrical circuit including a switching element, wherein the switching element preferably functions as an on/off switch so as to alternately increase the mechanical impedance of layers 26a and 26b.

Figure 8F:
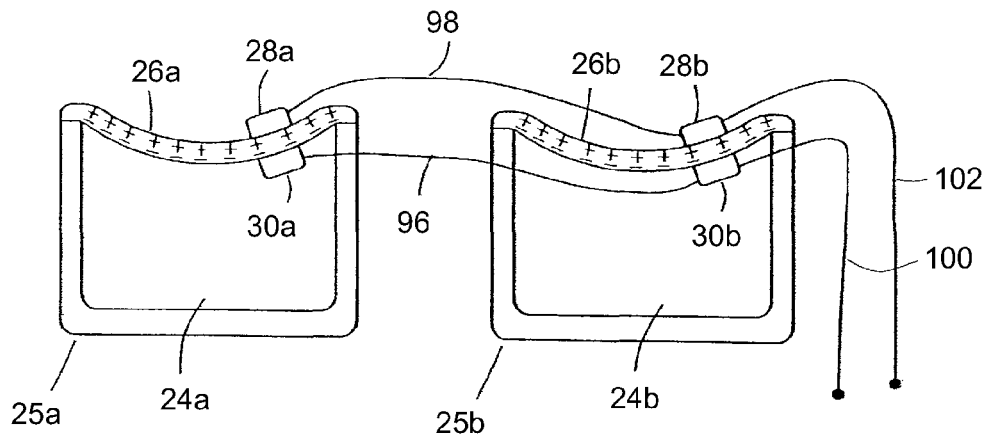

FIG. 8f shows another embodiment, wherein the first and second transducing cell members are interconnected by means of a parallel connection. As shown, electrodes 30a and 30b are interconnected by means of conducting line 96, electrodes 28a and 28b are interconnected by means of conducting line 98, and electrodes 30b and 28b are provided with conducting lines 100 and 102, respectively, the conducting lines for connection to an electrical circuit including a switching element. The switching element preferably functions as an on/off switch for alternately decreasing and increasing the mechanical impedance of layers 26a and 26b.

Figure 9:
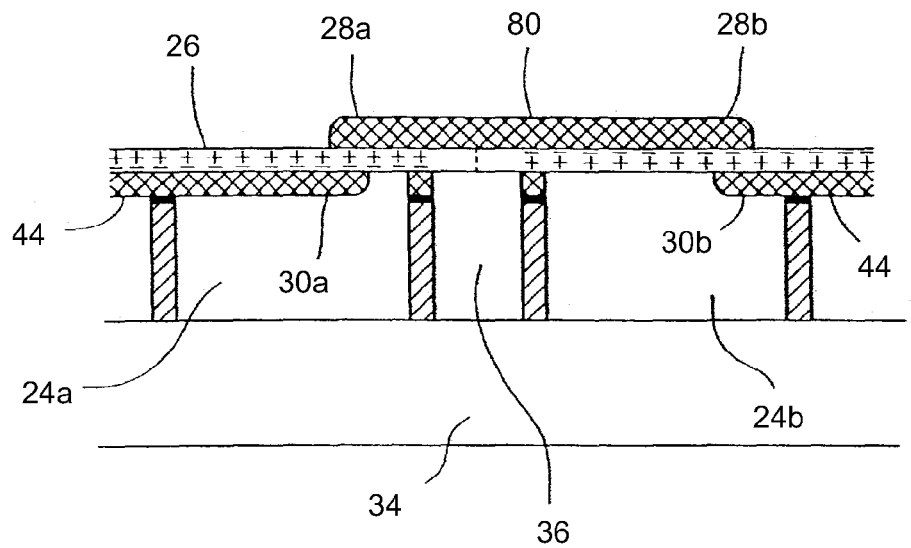
FIG. 9 is a longitudinal section of a transmitter element according to the present invention including an anti-parallel electrical connection.

FIG. 9 shows a possible configuration of two transducing cell members etched onto the same substrate and interconnected by means of an anti-parallel connection. As shown in the figure, the transducing cell members are covered by a common piezoelectric layer 26, wherein the polarity of the portion of layer 26 received between electrodes 30a and 28a is opposite to the polarity of the portion of layer 26 received between electrodes 30b and 28b. Electrodes 28a and 28b are bonded by means of a conducting line 80, and electrodes 30a and 30b are provided with conducting lines 44 for connection to an electrical circuit.

Figure 10:
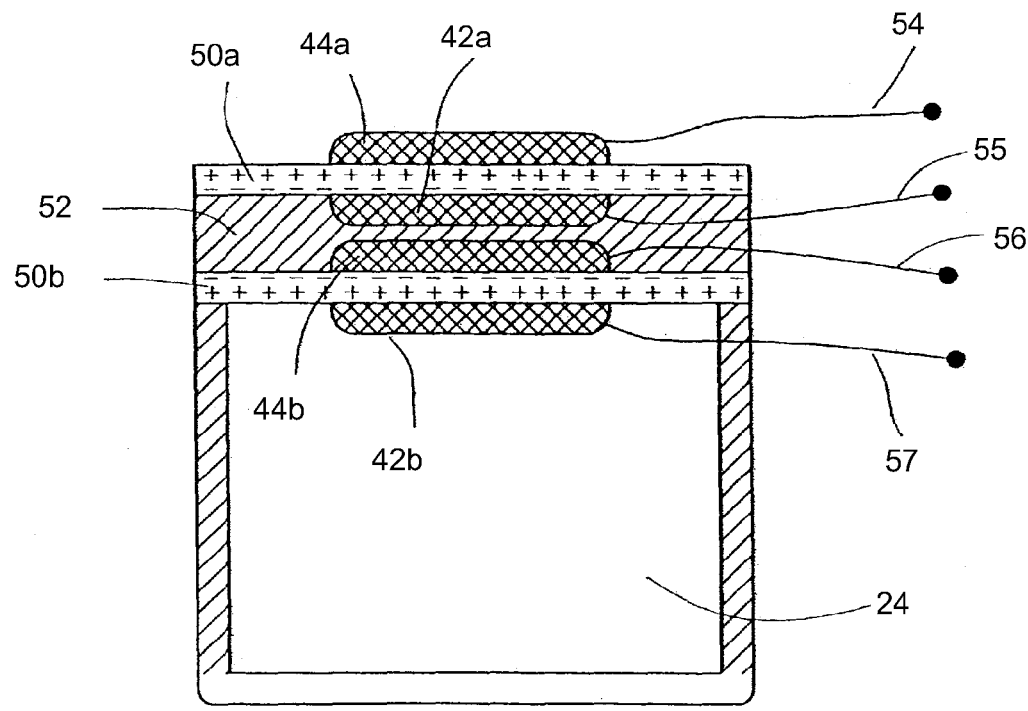
FIG. 10 is a longitudinal section of another embodiment of a transmitter element according to the present invention.

Another embodiment of a transmitter element according to the present invention is shown in FIG. 10. The transmitter element includes a transducing cell member having a cavity 24 covered by a first and second piezoelectric layers, 50a and 50b, preferably having opposite polarities. Preferably, layers 50a and 50b are interconnected by means of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of the present invention.

As mentioned hereinabove, in those embodiments in which the acoustic transducer 20 is used with device 10, the electrical signal generated by the acoustic transducer 20 can directly or indirectly activate the release of the molecules from reservoir 14.

Figure 11:
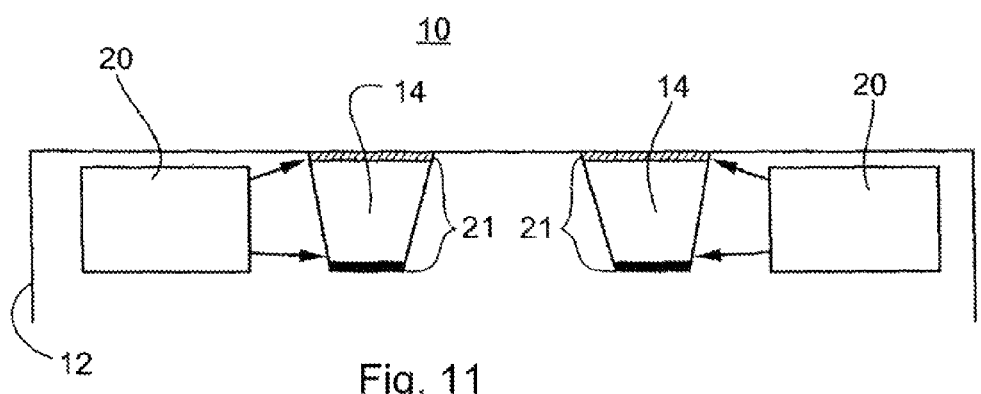
FIG. 11 illustrates a direct activation configuration of a molecule delivery device of the present invention.

In a direct activation embodiment of device 10 which is specifically shown in FIG. 11, the electrical signal generated by acoustic transducer 20 is communicated directly (via circuitry) to electrodes 21 to thereby generate the electrical potential.

It will be appreciated that in such cases, the degree of barrier permeabilization and as such the degree of drug release can be controlled by the duration and/or frequency of the acoustic signal and/or its intensity received by acoustic transducer 20.

It will further be appreciated that in cases where device 10 includes a plurality of reservoirs, several acoustic transducers can be utilized such that various activation schemes can be employed.

For example, device 10 can include a plurality of acoustic transducers 20 each dedicated to a specific reservoir of reservoirs 14. In such a case, each acoustic transducer 20 can function within a specific frequency range and as such activate release from a specific reservoir 14 only upon reception of an acoustic signal of a specific frequency or frequency range.

Such a configuration enables selective activation of specific reservoirs enabling control over the amount and rate of molecules released as well as enabling control over the type of molecules released, in cases where specific molecules are stored within specific reservoirs.

Figure 12:
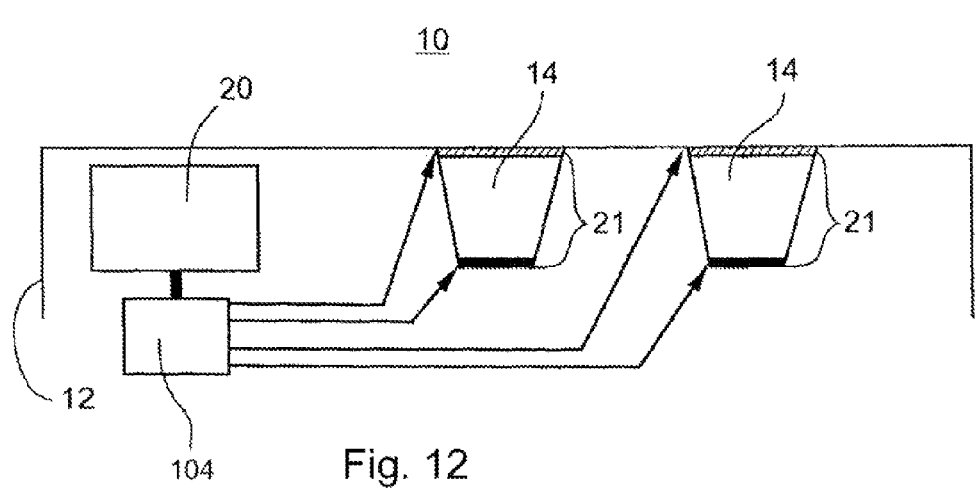
FIG. 12 illustrates an indirect activation configuration of a molecule delivery device of the present invention.

In an indirect activation embodiment of device 10 shown in FIG. 12, the electrical signal generated by acoustic transducer 20 serves to activate an energy storage device 104 which in turn generates the electrical potential between electrodes 21.

In such cases, acoustic transducer 20 preferably forms a part of an acoustic switch 106 which can be configured as described below.

Figure 13:
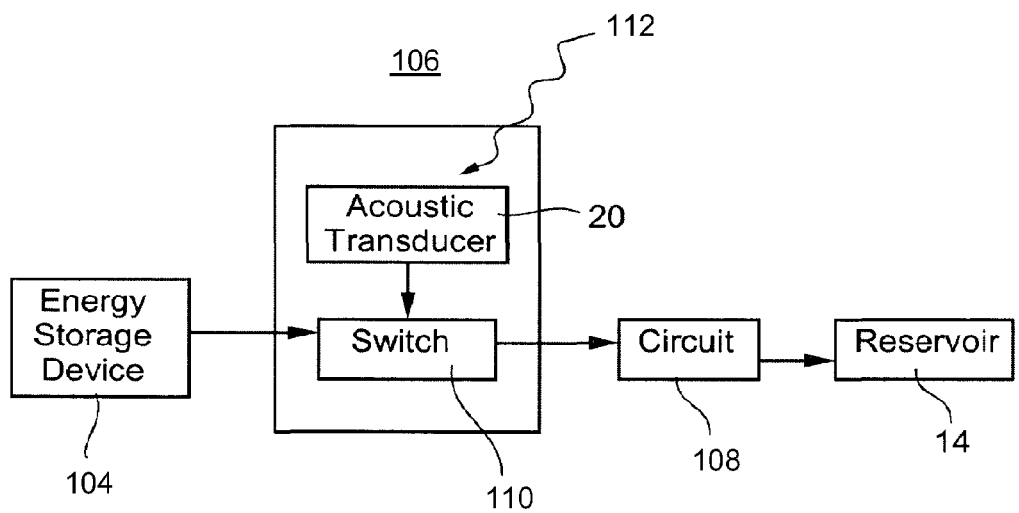
FIG. 13 is a schematic diagram illustrating an acoustic switch utilizable by a device of the present invention.

As specifically shown in FIG. 13, acoustic switch 106 includes an electrical circuit 108 configured for performing one or more functions or commands when activated.

Acoustic switch 106 further includes an energy storage device 104 (power source) and an acoustic transducer 20 coupled to electrical circuit 108 and energy storage device 104.

In addition, acoustic switch 106 also includes a switch 110, such as the switch described in the Examples section below, although alternatively other switches, such as a miniature electromechanical switch and the like (not shown) may be provided.

Energy storage device 104 may be any of a variety of known devices, such as an energy exchanger, a battery and/or a capacitor (not shown). Preferably, energy storage device 104 is capable of storing electrical energy substantially indefinitely. In addition, energy storage device 104 may be capable of being charged from an external source, e.g., inductively, as will be appreciated by those skilled in the art. In a preferred embodiment, energy storage device 104 includes both a capacitor and a primary, non-rechargeable battery. Alternatively, energy storage device 104 may include a secondary, rechargeable battery and/or capacitor that may be energized before activation or use of acoustic switch 106.

Acoustic switch 106 operates in one of two modes, a "sleep" or "passive" mode when not in use, and an "active" mode, when commanding electrical energy delivery from energy storage device 104 to electrical circuit 108 in order to activate release of molecules from reservoir 14 as described hereinabove.

When in the sleep mode, there is substantially no energy consumption from energy storage device 104, and consequently, acoustic switch 106 may remain in the sleep mode virtually indefinitely, i.e., until activated. Thus, acoustic switch 106 may be more energy efficient and, therefore, may require a smaller capacity energy storage device 104 than power switching devices that continuously draw at least a small amount of current in their "passive" mode.

To activate the acoustic switch, one or more external acoustic energy waves or signals 112 are transmitted until a signal is received by acoustic transducer 20. Upon excitation by acoustic wave(s) 112, acoustic transducer 20 produces an electrical output that is used to close, open, or otherwise activate switch 110. Preferably, in order to achieve reliable switching, acoustic transducer 20 is configured to generate a voltage of at least several tenths of a volt upon excitation that may be used as an activation signal to close switch 110.

As a safety measure against false positives (either erroneous activation or deactivation), switch 110 may be configured to close only upon receipt of an initiation signal followed by a confirmation signal. For example, an activation signal that includes a first pulse followed by a second pulse separated by a predetermined delay may be employed.

It will be appreciated that in the case of device 10 of the present invention, the use of a confirmation signal may be particularly advantageous since it can prevent unintentional release of drugs.

In addition to an activation signal, acoustic transducer 20 may be configured for generating a termination signal in response to a second acoustic excitation (which may be of different frequency or duration than the activation signal) in order to return acoustic switch 106 to its sleep mode.

For example, once activated, switch 110 may remain closed indefinitely, e.g., until energy storage device 104 is depleted or until a termination signal is received by acoustic transducer 20. Alternatively, acoustic switch 106 may include a timer (not shown), such that switch 110 remains closed only for a predetermined time, whereupon it may automatically open, returning acoustic switch 106 to its sleep mode.

Acoustic switch 106 may also include a microprocessor unit which serves to interpret the electrical signal provided from acoustic transducer 20 (e.g., frequency thereof) into a signal for switching switch 110.

Such interpretation enables to modulate the duration and strength of an electrical potential provided within reservoir 14 by simply varying the frequency and/or duration and/or intensity modulation of the acoustic signal provided from outside the body.

Additional acoustic switch configurations which are utilizable by the present invention are described in U.S. Pat. No. 6,628,989, the disclosure of which is expressly incorporated by reference as if fully set forth herein.

Device 10 of the present invention can form a part of a system for localized release of, for example, drugs, which is referred to herein as system 114.

Figure 14:
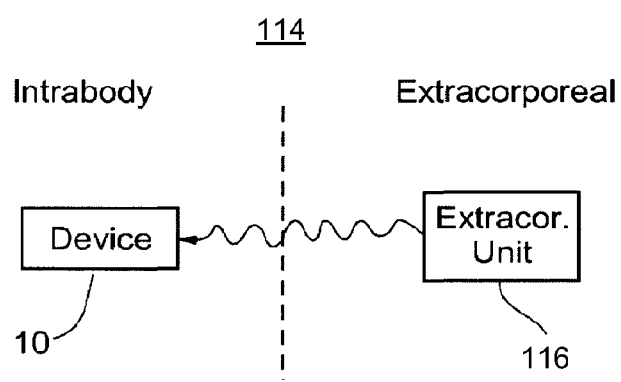
FIG. 14 is a black box diagram of a drug delivery system according to the teachings of the present invention.

As shown in FIG. 14, system 114 also includes an extracorporeal unit 116 which serves for generating an acoustic signal outside the body, which acoustic signal is received by device 10 implanted within the body. Numerous devices capable of generating an acoustic signal which can serve as extracorporeal unit 116 are known in the art, and as such no further description thereof is given herein.

System 114 can be used as follows. A device 10 filled with molecules is implanted within a specific body tissue. Following implantation, extracorporeal unit 116 generates an acoustic signal of a predetermined frequency and/or duration thereby activating release of the molecules from device 10 as described hereinabove.

Thus, the present invention provides a device, system and method useful for localized delivery of molecules such as drugs.

The device of the present invention provides several advantages over prior art devices such as those described in U.S. Pat. Nos. 6,123,861 and 5,797,898. Such advantages are afforded by the acoustic transducer component of the device which functions in converting an acoustic signal into an electrical activation signal.

In sharp contrast, the device described in U.S. Pat. Nos. 6,123,861 and 5,797,898, employs radiofrequency (RF) receivers which activate drug release upon reception of an RF signal generated outside the body. The use of RF activation is disadvantageous since RF signals are, at least in part, absorbed by body tissues and are directionally limited by bulky unidirectional antennas used for reception.

On the other hand, acoustic transducers, such as the one utilized by the device of the present invention, are omni-directional receivers which do not require antennas and as such do not suffer from structural and functional limitations which are inherent to RF receivers.

In addition, acoustic activation requires far less energy than RF activation since acoustic waves, unlike RF waves, propagate well within the aqueous medium which forms a substantial part of body tissues.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove find experimental support in the following examples.

EXAMPLES

Acoustic Switch Circuitry and Function

Figure 15:
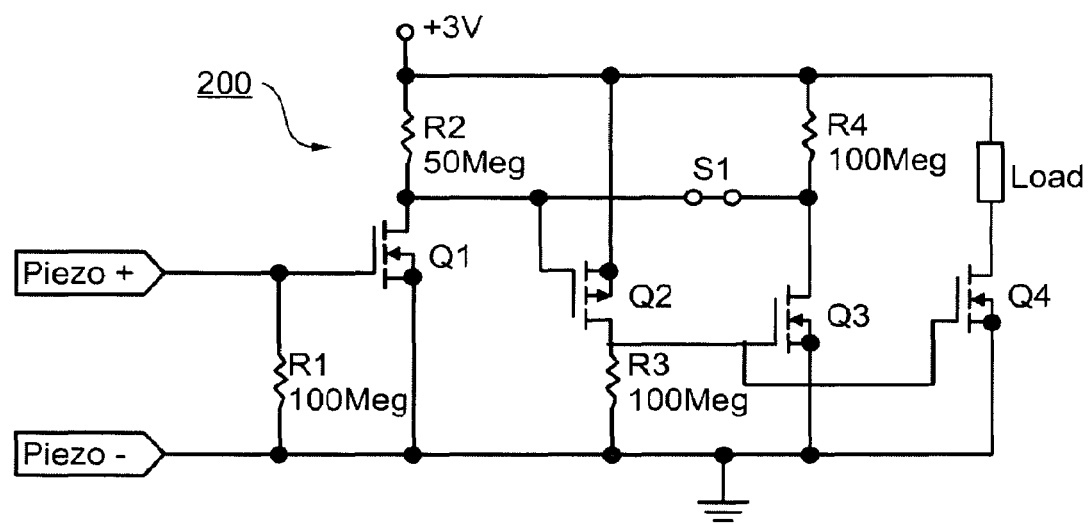
FIG. 15 is schematic diagram illustrating a control circuitry of the acoustic switch illustrated in FIG. 13.

Referring again to the drawings, FIG. 15, illustrates an example of circuitry and components employed by an acoustic switch 200 which is utilizable by the device of the present invention.

Switch 200 includes a piezoelectric transducer, or other acoustic transducer such the acoustic transducer described hereinabove (not shown, but connectable at locations piezo + and piezo −), a plurality of MOSFET transistors (Q1-Q4) and resistors (R1-R4), and switch S1.

In the switch's "sleep" mode, all of the MOSFET transistors (Q1-Q4) are in an off state. To maintain the off state, the gates of the transistors are biased by pull-up and pull-down resistors. The gates of N-channel transistors (Q1, Q3 & Q4) are biased to ground and the gate of P-channel transistor Q2 is biased to +3V. During this quiescent stage, switch S1 is closed and no current flows through the circuit.

Therefore, although an energy storage device (not shown, but coupled between the hot post, labeled with an exemplary voltage of +3V, and ground) is connected to the switch 200, no current is being drawn-therefrom since all of the transistors are quiescent.

When the piezoelectric transducer detects an external acoustic signal, e.g., having a particular frequency such as the transducer's resonant frequency, the voltage on the transistor Q1 will exceed the transistor threshold voltage of about one half of a volt. Transistor Q1 is thereby switched on and current flows through transistor Q1 and pull-up resistor R2. As a result of the current flow through transistor Q1, the voltage on the drain of transistor Q1 and the gate of transistor Q2 drops from +3V substantially to zero (ground). This drop in voltage switches on the P-channel transistor Q2, which begins to conduct through transistor Q2 and pull-down resistor R3.

As a result of the current flowing through transistor Q2, the voltage on the drain of transistor Q2 and the gates of transistors Q3 and Q4 increases from substantially zero to +3V. The increase in voltage switches on transistors Q3 and Q4. As a result, transistor Q3 begins to conduct through resistor R4 and main switching transistor Q4 begins to conduct through the "load," thereby switching on the electrical circuit.

As a result of the current flowing through transistor Q3, the gate of transistor Q2 is connected to ground through transistor Q3, irrespective of whether or not transistor Q1 is conducting. At this stage, the transistors (Q2, Q3 & Q4) are latched to the conducting state, even if the piezoelectric voltage on transistor Q1 is subsequently reduced to zero and transistor Q1 ceases to conduct. Thus, main switching transistor Q4 will remain on until switch S1 is opened.

In order to deactivate or open switch 200, switch S1 must be opened, for example, while there is no acoustic excitation of the piezoelectric transducer. If this occurs, the gate of transistor Q2 increases to +3V due to pull-up resistor R2. Transistor Q2 then switches off, thereby, in turn, switching off transistors Q3 and Q4. At this stage, switch 200 returns to its sleep mode, even if switch SI is again closed. Switch 200 will only return to its active mode upon receiving a new acoustic activation signal from the piezoelectric transducer.

It should be apparent to one of ordinary skill in the art that the above-mentioned electrical circuit is not the only possible implementation of a switch for use with the present invention. For example, the switching operation may be performed using a CMOS circuit, which may draw less current when switched on, an electromechanical switch, and the like.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. An implantable medical device, comprising:
    an acoustic transducer configured to receive an acoustic interrogation signal; and
    a means for modulating a reflected acoustic wave from the acoustic transducer, the reflected acoustic wave including data to be transmitted from the implantable medical device.

2. The implantable medical device of claim 1, wherein the means for modulating a reflected acoustic wave comprises a switching element coupled to the acoustic transducer.

3. The implantable medical device of claim 2, wherein the acoustic transducer includes a piezoelectric layer, and wherein the switching element is configured to controllably change the mechanical impedance of the piezoelectric layer based on the data.

4. The implantable medical device, of claim 2, further comprising a sensor configured for sensing at least one parameter and generating an electrical sensor signal, and wherein the switching element is configured to controllably change the mechanical impedance of the piezoelectric layer based on the frequency of the electrical sensor signal.

5. The implantable medical device of claim 1, wherein the acoustic transducer is configured to convert the acoustic interrogation signal into an electrical signal for providing electrical power to one or more components of the implantable medical device.

6. The implantable medical device of claim 1, wherein the acoustic transducer comprises:
   a cell member including at least one cavity;
   a flexible piezoelectric layer coupled to the cell member, the piezoelectric layer having an external surface and an internal surface; and
   a first electrode attached to the external surface of the piezoelectric layer and a second electrode attached to the internal surface of the piezoelectric layer.

7. The implantable medical device of claim 6, wherein the piezoelectric layer has a resonance at or near a wavelength of the acoustic interrogation signal.

8. The implantable medical device of claim 7, wherein the piezoelectric layer has a flexibility such that the resonant wavelength is larger than a dimension of the acoustic transducer.

9. The implantable medical device of claim 6, wherein the piezoelectric layer has a concave shape.

10. The implantable medical device of claim 6, wherein the cavity includes a gas.

11. The implantable medical device of claim 6, wherein at least one of the first and second electrodes covers only a portion of a surface of the piezoelectric layer.

12. An implantable medical device, comprising:
   at least one sensor configured for sensing at least one parameter of a physiological condition and for generating an electrical sensor signal representative of the physiological condition;
   an acoustic transducer coupled to the at least one sensor, the acoustic transducer configured to convert a received acoustic interrogation signal into an electrical signal;
   a means for modulating a reflected acoustic wave from the acoustic transducer based on the electrical sensor signal, the reflected acoustic wave including one or more encoded sensor measurements sensed by the at least one sensor.

13. The implantable medical device of claim 12, wherein the means for modulating a reflected acoustic wave comprises a switching element coupled to the acoustic transducer.

14. The implantable medical device of claim 13, wherein the acoustic transducer includes a piezoelectric layer, and wherein the switching element is configured to controllably change the mechanical impedance of the piezoelectric layer based on the frequency of the electrical sensor signal.

15. The implantable medical device of claim 12, wherein the acoustic transducer is configured to convert the acoustic interrogation signal into an electrical signal for providing electrical power to one or more components of the implantable medical device.

* * * * *